(12) United States Patent
Goldman

(10) Patent No.: US 10,912,513 B2
(45) Date of Patent: Feb. 9, 2021

(54) PRESSURE AND VACUUM SENSORS, SYSTEMS, AND ASSOCIATED METHODS WITH A PLURALITY OF LAYERS OF A DIELECTRIC MATERIAL

(71) Applicant: WOUND CARE AND REHAB MEDICINE LLC, Sun Prairie, WI (US)

(72) Inventor: Robert J. Goldman, Aston, PA (US)

(73) Assignee: WEARSENSE LLC, Aston, PA (US)

(*) Notice: Subject to any disclaimer, the term of this patent is extended or adjusted under 35 U.S.C. 154(b) by 0 days.

(21) Appl. No.: 16/303,162

(22) PCT Filed: May 26, 2017

(86) PCT No.: PCT/US2017/034658
§ 371 (c)(1),
(2) Date: Nov. 20, 2018

(87) PCT Pub. No.: WO2017/205728
PCT Pub. Date: Nov. 30, 2017

(65) Prior Publication Data
US 2019/0216394 A1    Jul. 18, 2019

Related U.S. Application Data

(60) Provisional application No. 62/341,783, filed on May 26, 2016.

(51) Int. Cl.
*A61B 5/00* (2006.01)
*A61B 5/103* (2006.01)

(52) U.S. Cl.
CPC .......... *A61B 5/6807* (2013.01); *A61B 5/1036* (2013.01); *A61B 5/6828* (2013.01);
(Continued)

(58) Field of Classification Search
None
See application file for complete search history.

(56) References Cited

U.S. PATENT DOCUMENTS 4,490,773 A * 12/1984 Moffatt .................... H01G 5/16
361/283.4
7,208,960 B1 * 4/2007 Deangelis ............ G01D 5/2405
324/661
(Continued)

FOREIGN PATENT DOCUMENTS

WO    2016/073777 A1    5/2016

OTHER PUBLICATIONS

International Search Report/Written Opinion dated Jul. 25, 2017, in corresponding International Application No. PCT/US2017/034658.

*Primary Examiner* — Peter J Macchiarolo
*Assistant Examiner* — Jermaine L Jenkins
(74) *Attorney, Agent, or Firm* — Duane Morris LLP

(57) ABSTRACT

A system includes a housing, a capacitive sensor, and an electronics module. The housing has an interior and is configured to be maintained at a first pressure that is lower than a pressure external of the housing the interior under a vacuum pressure. The capacitive sensor is disposed within the housing and includes a plurality of layers of a dielectric material. The electronics module is coupled to the capacitive sensor and includes a processor configured to receive a raw capacitance value from the capacitive sensor and to output a signal identifying a pressure exerted on the capacitive sensor.

20 Claims, 34 Drawing Sheets

(52) U.S. Cl.
CPC .......... *A61B 5/6831* (2013.01); *A61B 5/6887* (2013.01); *A61B 5/002* (2013.01); *A61B 5/6892* (2013.01); *A61B 2503/10* (2013.01); *A61B 2505/03* (2013.01); *A61B 2505/07* (2013.01); *A61B 2505/09* (2013.01); *A61B 2562/0247* (2013.01); *A61B 2562/12* (2013.01)

(56) References Cited

U.S. PATENT DOCUMENTS

| | | | | |
|---|---|---|---|---|
| 7,301,351 | B2* | 11/2007 | Deangelis | G01D 5/2405 |
| | | | | 324/658 |
| 7,395,717 | B2* | 7/2008 | DeAngelis | G01L 1/146 |
| | | | | 73/724 |
| 7,719,007 | B2* | 5/2010 | Tompkins | G01L 1/142 |
| | | | | 257/48 |
| 8,609,564 | B2* | 12/2013 | Matsuda | H01G 4/1227 |
| | | | | 264/615 |
| 8,858,746 | B2* | 10/2014 | Ishihara | H01G 13/00 |
| | | | | 156/89.11 |
| 8,919,211 | B1* | 12/2014 | Hanson | G01L 1/146 |
| | | | | 73/862.626 |
| 10,186,377 | B2* | 1/2019 | Fujii | H01G 4/30 |
| 10,234,340 | B2* | 3/2019 | Severinkangas | G01L 1/146 |
| 2011/0054359 | A1 | 3/2011 | Sazonov et al. | |
| 2014/0200584 | A1 | 7/2014 | Stein et al. | |
| 2014/0296749 | A1 | 10/2014 | Reid, Jr. et al. | |
| 2016/0029956 | A1 | 2/2016 | Rowland et al. | |
| 2016/0293333 | A1* | 10/2016 | Kaneko | H01G 4/12 |
| 2017/0079868 | A1* | 3/2017 | Reid, Jr. | A61B 5/0053 |
| 2017/0265978 | A1* | 9/2017 | Borotto | A61C 19/05 |
| 2018/0206746 | A1* | 7/2018 | Narasimhan | A61B 5/02241 |
| 2018/0256071 | A1* | 9/2018 | Mathieu | A43B 3/0005 |

* cited by examiner

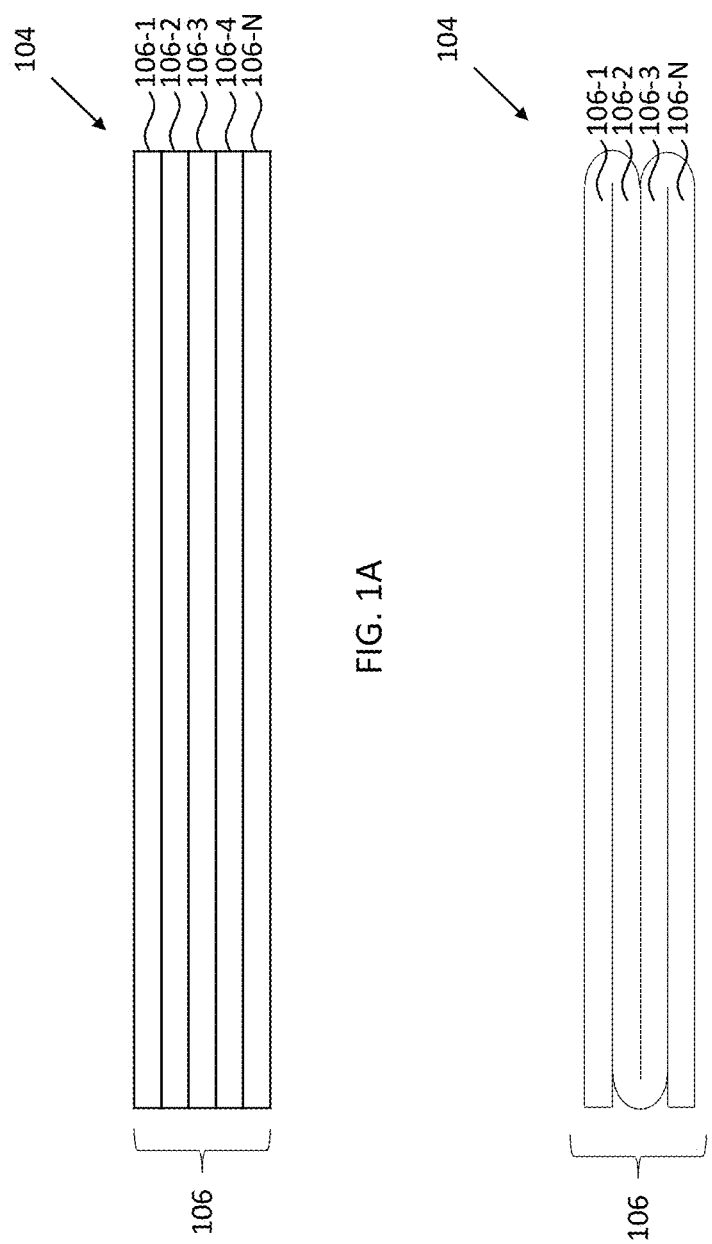

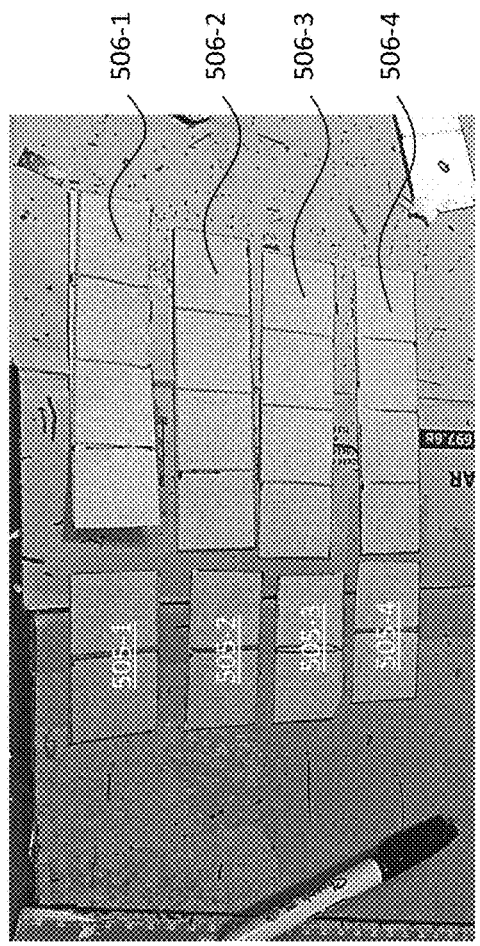
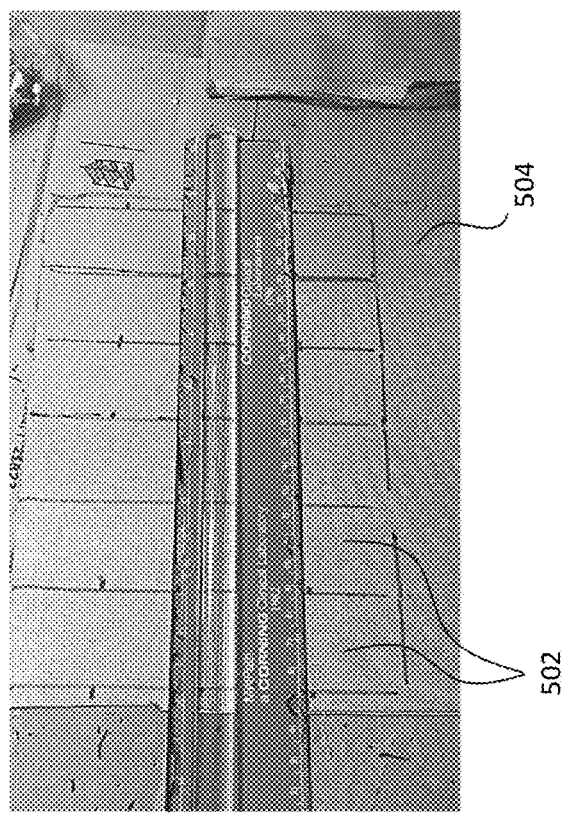
FIG. 5A
FIG. 5B

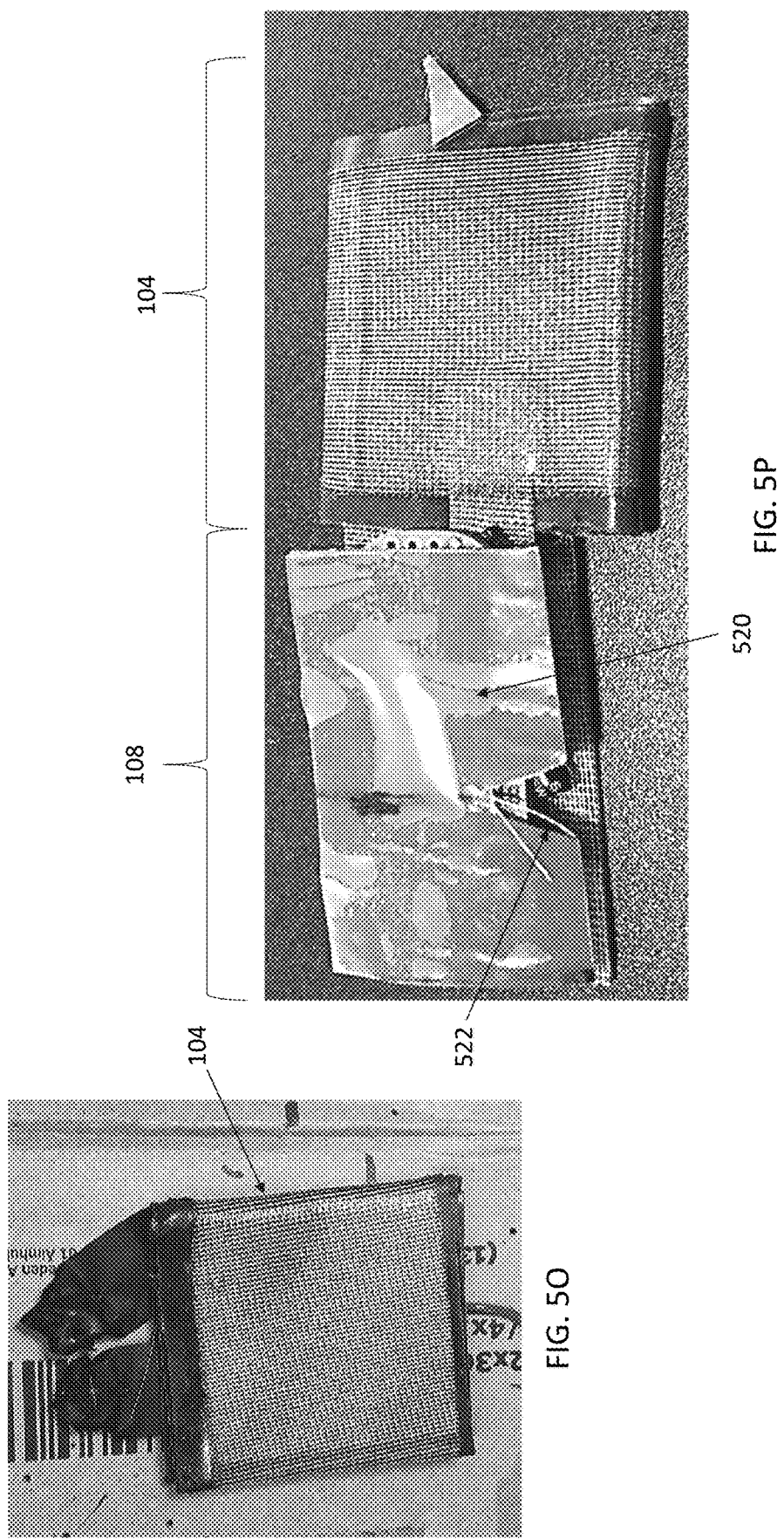

PRESSURE AND VACUUM SENSORS, SYSTEMS, AND ASSOCIATED METHODS WITH A PLURALITY OF LAYERS OF A DIELECTRIC MATERIAL

CROSS-REFERENCE TO RELATED APPLICATIONS

This application is a national phase application under 35 U.S.C. § 371 of International Patent Application No. PCT/US2017/034658, which was filed May 26, 2017 claiming priority to U.S. Provisional Patent Application No. 62/341,783, filed May 26, 2016, the entireties of which are incorporated by reference herein.

COPYRIGHT/MASK WORK NOTICE

A portion of the disclosure of this patent document contains material which is subject to copyright or mask work protection. The copyright or mask work owner has no objection to the facsimile reproduction by anyone of the patent document or the patent disclosure, as it appears in the Patent and Trademark Office patent file or records, but otherwise reserves all copyright or mask work rights whatsoever.

BACKGROUND

The disclosed devices, systems, and methods can be used in medicine. More particularly, the disclosed devices, systems, and methods relate to sensors, sensor systems, and associated methods that can be used to provide biofeedback for aiding in wound care and/or physical training.

Biofeedback may be provided for monitoring the weight applied to a limb ("limb-load monitoring"). For example, total hip replacements alone are performed 200,000 times per year in the United States, and such surgeries, a patient may have certain limitations to the amount of weight the patient can put on a foot, leg, or hip. In such scenarios, surgeons typically prescribe "toe-touch" or "partial" weight bearing. Partial weight bearing continues until healing has progressed sufficiently to allow full weight bearing safely. In almost all rehabilitation centers there is no way to assure compliance with these orders except by observation. Due to the absence of suitable devices, the true cost of excessive weight bearing has never been systematically studied. However, it is reasonable to hypothesize that un-monitored weight bearing prolongs healing time, duration of hospitalization, and dependent status. Limb load monitoring could significantly reduce this apparent loss of time and money. There are various other medical scenarios in which it would be helpful for a surgeon, physician or patient to understand the amount of pressure exerted on a patient, such as on a limb, joint, or other surface.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 1A is a cross-sectional diagram of one example of individual layers of a capacitive sensor in accordance with some embodiments;

FIG. 1B is a cross-sectional diagram of another example of a plurality of layers of a capacitive sensor achieved by folding a single layer of material over on itself in accordance with some embodiments;

DETAILED DESCRIPTION

Figure 1:
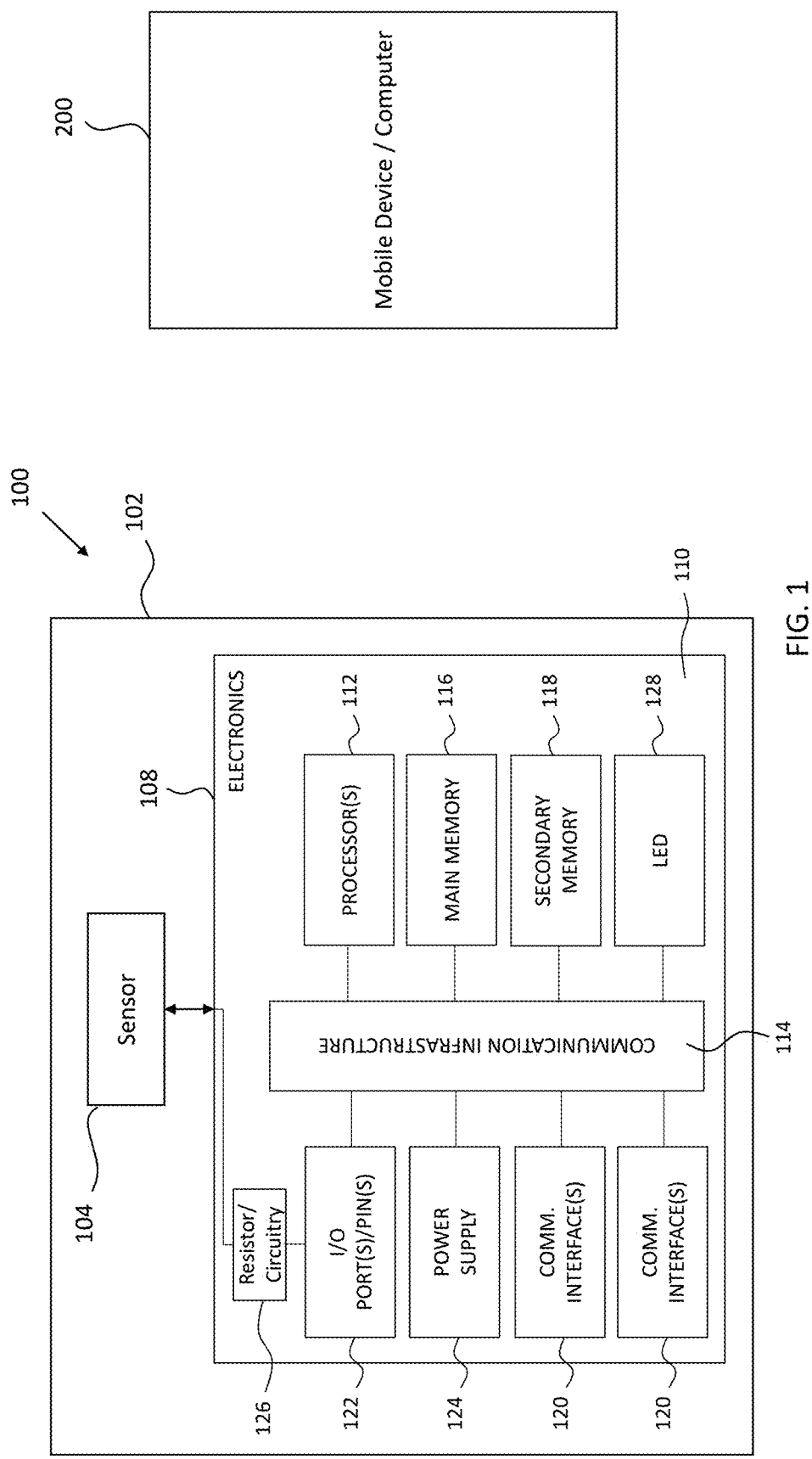
FIG. 1 is a block diagram of one example of a sensor system and an associated device in accordance with some embodiments.

The following disclosure provides many different embodiments, or examples, for implementing different features of the subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The disclosed systems and methods advantageously enable provides for the sensing of pressure and/or a vacuum at the surface of the skin or other bodily surface. In some embodiments, a pressure-sensing system includes a dielectric foam without memory such that the capacitance returns to its original, baseline value after any compressive force on the dielectric is removed or abated. Advantageously, the dielectric foam is flexible, non-toxic, and inexpensive while also being accurate and nonobtrusive. The inclusion of the flexible dielectric provides for a sensor that expands the function of conventional polyurethane capacitive sensors to be able to able to measure pressure or vacuum while retaining its fabric-like nature.

In some embodiments, the disclosed systems provide feedback for rehabilitation and wound care patients in addition to helping athletes reach set goals. Each system can be fabricated with microminiaturize electronics in a vacuum seal making it linear, well protected, and stable. The systems are hypoallergenic and work well next to the skin of a patient.

FIG. 1 illustrates one example of a sensing system 100 in accordance with some embodiments. System 100 includes an outer packaging or housing 102 having an interior in which a sensor 104, including a plurality of layers 106-N, and electronics or circuit board 108 can be disposed. For example, in some embodiments, only sensor 104 is disposed within housing 102 and the electronics or circuit board 108 are disposed external of housing 102 and are coupled to sensor 104 wirelessly or by a physical connector such as cabling, leads, wires, or the like. In some embodiments, outer packaging or housing 102 is a flexible bag that is sealed to maintain a pressure of the interior of the housing to be less than a pressure outside of the housing. Examples of the materials of outer packaging or housing include, but are not limited to low density polyethylene (LDPE), polyethelene terephthalate (i.e polyester, PET), BoPET (Bi-axially-oriented polyethylene terephthalate, also known as Mylar or Melinex). Mylar has a low oxygen permeability coefficient (0.035), but low density polyethelene is much more porous (oxygen permeability of 2.2). For this reason, polyethelene is laminated in multiple layers with thermoplastic polyamide (nylon) to make flexible clear food package bags. In some embodiments, the thickness of the housing 102 is approximately 0.005 inches (0.127 mm); however, one of ordinary skill in the art will understand the thickness of the housing 102 can vary such that housing 102 can be thicker or thinner depending on the type of material used. Additionally, in some embodiments, housing 102 can be formed from a more rigid material that provides an airtight closure capable of maintaining its interior at a pressure that is less than the ambient pressure, i.e., the pressure external to housing 102.

The pressure of the interior of the vacuum sealed housing 102 can be selected based on the material utilized for the sensor 104 as discussed below. The vacuum pressure of the interior of housing 102 can be obtained using any suitable vacuum device. An example of one such suitable vacuum device is the VacMaster® VP112S available from Ary Inc. of Overland Park, Kans. This is a chamber vacuum device, and produces a vacuum of 12-13.5 PSI. Another is Foodsaver system V2865. This is a so-called "slot sealer" that uses a bag constructed of nylon-LDPE laminate with the LDPE meshed to allow air flow. The higher the resistance to air flow, the lower the vacuum. The vacuum created is 10 PSI or less. Using either of these systems, the vacuum pressure of the interior housing 102 can range from 3-14 PSI although one of ordinary skill in the art will understand that the vacuum pressure of the interior housing 102 can be greater or less than this range depending on other factors, including number of layers 106 of the sensor 104 and material of the layers 106. Note that, in some embodiments, the vacuum will typically not exceed 14.7 PSI which is the ambient air pressure at sea level.

Sensor 104 is a capacitive sensor that provides an output value that changes as a function of force, pressure, or vacuum. Examples of suitable capacitive sensors 104 include, but are not limited to, sensors disclosed in U.S. Pat. Nos. 5,662,123; 5,449,002; 5,775,332; 6,033,370; 6,616,579; 6,595,901; 6,925,851; and 7,384,380, the entireties of which are incorporated by reference herein. In some embodiments, the sensor 104 is a laminate formed from a plurality of distinct electrically-connected layers 106-1: 106-N (collectively "layers 106") as best seen in FIG. 1A. In some embodiments, the number of layers, N, is equal to five, although fewer or more layers 106 can be implemented. The individual layers 106 of the sensor 104 can be polyurethane, polychloroprene (i.e., neoprene), polyethelene (i.e, plastizote, pelite, aliplast), or other collapsible dielectric foam material as will be understood by one of ordinary skill in the art. In some embodiments, such as the embodiment shown in FIG. 1B, the layers 106 are formed from a single piece of material that is folded over itself to provide the desired thickness and/or number of layers. For example, a single piece of material can be folded three times to provide four layers as shown in FIG. 1B.

In some embodiments, at least one of the plurality of layers 106 of sensor 104 is an open-cell foam material, such as type 30 (very soft) PORON®, available from the Rogers Corporation of Rogers, Conn. In some embodiments, for example, the thickness of the open cell foam material layer is approximately 0.035 inches (0.889 mm); however, one of ordinary skill in the art will understand that layers of dielectric material can be thicker or thinner. An open-cell foam material has a force-deflection or stress-strain relationship with three phases, each having distinct advantages. For example, the open-cell foam material provides an increased force required to collapse the walls of cells, a more linear middle phase in which cell walls decrease in height in an even manner, and a collapse stage in which the cells "bottom out" thereby increasing the stress needed to produce a strain as described in greater detail elsewhere herein.

Figure 1C:
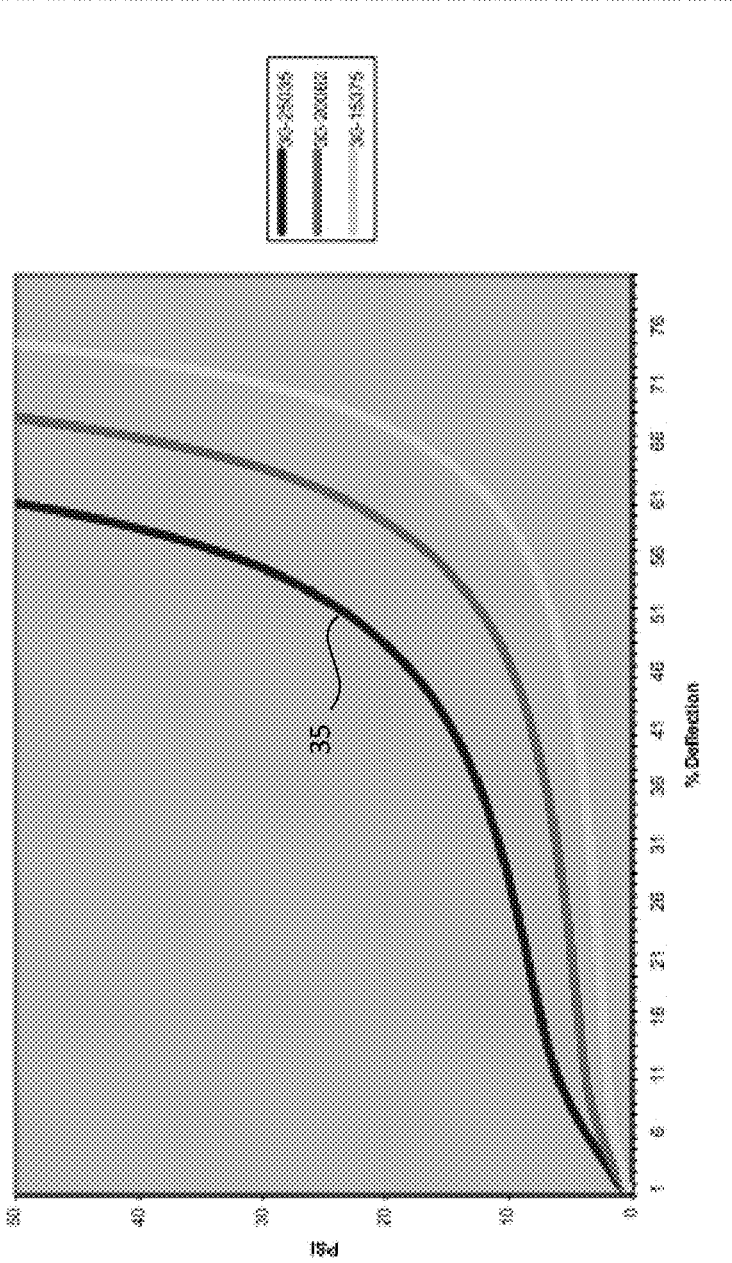
FIG. 1C is a pressure versus percent deflection plot for one example of a material that can be used as one or more layers of a multi-layer sensor in accordance with some embodiments.

These phases can be seen in FIG. 1C, which is one example of a graph depicting the stress-strain relationship for various PORON® polyurethane foams obtained from Rodgers Corporation. As shown in FIG. 1C, putting a type 30 foam of 0.035 inches (0.889 mm) under a vacuum of approximately 7-10 pounds per square inch ("PSI"), which is identified by line 35 in FIG. 1C (the other lines can be ignored for purposes of this discussion), provides for more linearity compared to a foam not put under vacuum (i.e., 0 PSI). However, one of ordinary skill in the art will appreciate that different foam materials may have different stress-strain characteristics and therefore the selected vacuum pressure within housing 102 will be adjusted accordingly. Indeed, FIG. 1C also illustrates linearity around a "zero baseline." The zero baseline is the "pressure bias" exerted on the sensor after evacuation. Around this zero baseline the sensor detects and reports much smaller pressure changes The electronics 108 are coupled to the sensor 104 and are configured to receive a signal from sensor 104, perform certain calculations, and provide an output to another device 200, such as a mobile phone, or computer, and/or server, to list only a few possibilities. In some embodiments, the electronics 108 are provided on a single board, however, electronics 108 can be provided on a plurality of boards that are communicatively and/or physically coupled to one another.

Referring again to FIG. 1, the various components of electronics 108 on a circuit board 110 in accordance with some embodiments are now discussed. Electronics 108 includes one or more processors, such as processor(s) 112. Processor(s) may be any central processing unit (CPU), microcontroller, or other computational device, circuit, or logic, for executing instructions. Processor(s) 112 are connected to a communication infrastructure 114 (e.g., a communications bus, cross-over bar, or network).

Electronics 108 also include a main memory 116, such as a random access ("RAM") memory, and may also include a secondary memory 118. Secondary memory 110 may include a more persistent memory such as, for example, a hard disk drive ("HDD") 118 and/or removable storage drive (not shown), such as a secure digital ("SD") slot and card, removable memory chip (such as an erasable programmable read only memory ("EPROM")), programmable read only memory ("PROM")), and corresponding interface, which allow software and data to be transferred from the removable storage unit 118 to processor(s) 112.

Electronics 108 also include one or more communication interface(s) 120, which allow software and data to be transferred between electronics 108 and other devices, such as, for example, a mobile device or computer 200 that may be locally or remotely connected to system 100. Examples of the one or more communication interface(s) 120 may include, but are not limited to, a modem, a network interface (such as an Ethernet card or wireless card), a communications port, a Personal Computer Memory Card International Association ("PCMCIA") slot and card, one or more Personal Component Interconnect ("PCI") Express slot and cards, a Universal Serial Bus (USB) port, or any combination thereof. The one or more communication interfaces 120 may also include a wireless interface configured for short range communication, such as near field communication ("NFC"), Bluetooth, or other interface for communication via another wireless communication protocol.

Software and data transferred via the one or more communications interfaces 120 are in the form of signals, which may be electronic, electromagnetic, optical, or other signals capable of being received by communications interface(s) 120. These signals are provided to communications interface(s) 120 via a communications path, channel, or link. The path, channel, or link may be implemented using wire or cable, fiber optics, a telephone line, a cellular link, a radio frequency ("RF") link, or other communication channels. Although the communications interface(s) are illustrated as a single block, one of ordinary skill in the art will understand that the communications interface(s) can include a number of separate chips that are coupled to communications infrastructure 114.

In this document, the terms "non-transitory computer program medium" and "non-transitory computer readable medium" refer to media such as removable storage units or a hard disk installed in hard disk drive. These computer program products provide software to processor(s) 112. Computer programs (also referred to as "computer control logic") may be stored in main memory 116 and/or secondary memory 118. Computer programs may also be received via the one or more communications interfaces 120. Such computer programs, when executed by a processor(s) 112, enable the system 100 to perform the features of the method discussed herein.

In an embodiment where the method is partially or entirely implemented using software, the software may be stored in a computer program product and loaded into system 100 using removable storage drive, hard drive, and/or communications interface(s) 120. The software, when executed by processor(s) 112, causes the processor(s) 112 to perform the functions of the method described herein. In another embodiment, the method is implemented primarily in hardware using, for example, hardware components such as application specific integrated circuits ("ASICs"). Implementation of the hardware state machine so as to perform the functions described herein will be understood by persons skilled in the art. In yet another embodiment, the method is implemented using a combination of both hardware and software.

Still referring to FIG. 1, electronics 108 may also include a number of input/output ("I/O") ports or pins 122. In some embodiments, the I/O ports or pins are coupled to a resistor 126 or other circuitry or chips (as described below) that couples the electronics 108 to sensor 102. Electronics on circuit board(s) 110 also can include a light emitting diode ("LED") 128 or other visual indicator and a power supply 124, such as a replaceable and/or rechargeable battery as will be understood by one of ordinary skill in the art. In some embodiments, power supply 124 includes a 3-volt Lithium battery. A rechargeable battery can be recharged by connecting to another power supply, such as a wall outlet or computer, by way of a USB interface and/or another power interface or jack (not shown).

Figure 1D:
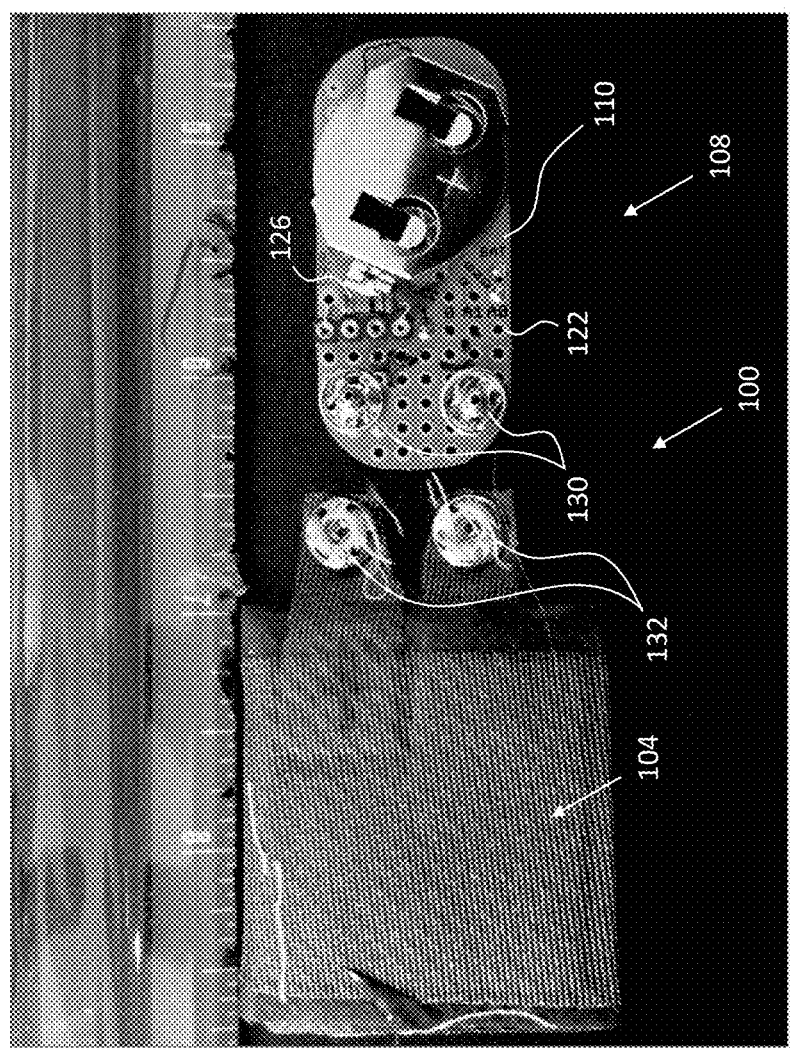
FIG. 1D illustrates one example of certain components of a sensor system in accordance with some embodiments.

In some embodiments, electronics 108 include an ATmega 48A of Arduino design running C code which interfaces with a CC2540 Bluetooth system-on-chip (SoC), both of which are contained on a Light Blue Bean board, available from Punch Through Design, LLC of San Francisco, Calif. For example, FIG. 1D is a photograph illustrating one example of a sensor system 100, including a sensor 102 and associated electronics 108 in the form of an ATmega 48A and Light Blue Bean boards on a circuit board 110. A resistor 126 is coupled to circuit board 110 in series with sensor 102 for quantifying the capacitance. In some embodiments, resistor 126 can be implemented as a resistor having a resistance of 2 MΩ; however, one of ordinary skill in the art will understand that the resistance of resistor 126 can vary.

A pair of mechanical and electrical fasteners 130 are soldered to the I/O ports 122 of circuit board 110 and are used to electrically and mechanically couple electronics 108 to sensor 102 via the mechanical and electrical fasteners 132 of sensor 104. In the embodiment shown in FIG. 1D, the mechanical and electrical fasteners 130, 132 are in the form of metallic snaps with the snaps 132 of the sensor 104 being sewn to a strip of conductive carbon that is reinforced by conductive transfer tape and conductive silver cloth, which is then coupled to silver fabric "plates" or panels as described in greater detail below. Although not readily identifiable in FIG. 1D, the Light Blue Bean board includes at communications interface 120 in the form of a Bluetooth interface CC2540 Bluetooth SoC, for utilizing the Bluetooth Low Energy ("BLE") signal protocol. Although the BLE signal protocol is referenced herein, one of ordinary skill in the art will understand that other Ultra Low Power (ULP) communication protocols can be used, such as ANT or ANT+ to list only a couple of possibilities. In some embodiments, the Bluetooth interface is configured to transfer a calculated force signal to another device 200, such as a mobile device, computer, or network server, such as a Raspberry Pi device that utilizes a NODE RED or similar protocol consistent with the Internet-of-Things (IoT) standards, or any other device that is equipped with a corresponding communications interface to the communications interface 120 utilized by system 100 for transferring the force signal.

As mentioned above, in some embodiments, circuitry 126 does not include a resistor 126, but instead includes other integrated circuitry or chips. For example, in some embodiments, circuitry 126 of electronics 108 include one or more 555 timers or other chip, circuitry, or module configured to output one or more pulses to an active lead of sensor 104. A first 555 timer can be configured to operate in a stable mode, and a second 555 timer can be configured to operate in a monostable mode. In such embodiments, the 555 timer operating in the monostable mode has a pulse width that increases with increasing sensor capacitance. The increased capacitance causes an increased duty cycle as well, which in turn increases the voltage through a low-pass filter or integrator circuit that can be provided on electronics board 108. The analog signal output from the low-pass filter/integrator circuit is received by processor(s) that then converts the signal to an output value that is indicative of the pressure on sensor 104. One of ordinary skill in the art will understand that the foregoing descriptions of electronics are not considered limiting and that any number of other ways in which electronics 108 transmit pulses to sensor 104 and then receive a raw capacitance signal from sensor 104 can be implemented.

Figure 2:
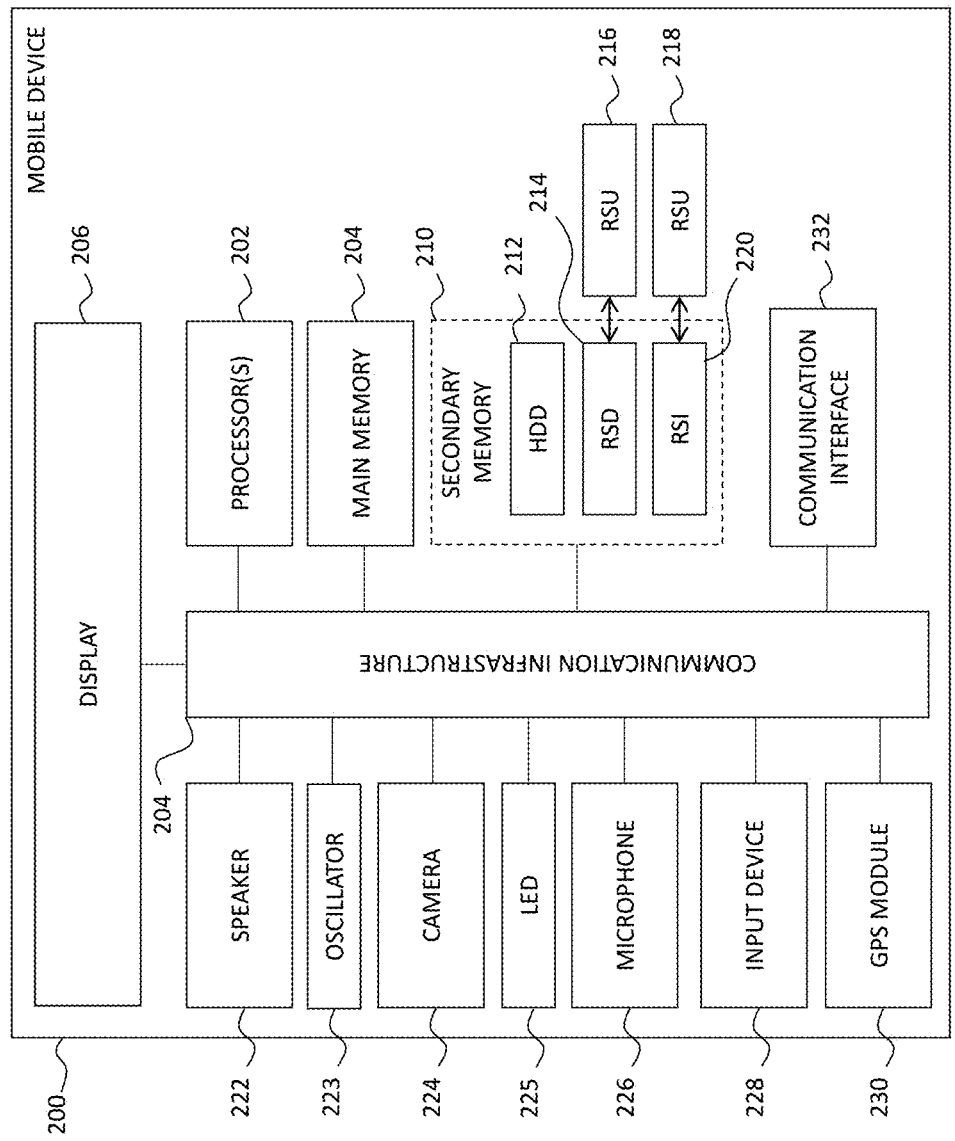
FIG. 2 is a block diagram of the functional components of one example of a mobile device that can communicate with a sensor system in accordance with some embodiments.

One of ordinary skill in the art will understand that such remote device 200, which can take the form of a mobile device, e.g., a cellular phone or table, a computer, server, communications relay, or other device, can include additional components which are illustrated in the block diagram of FIG. 2. Although FIG. 2 is discussed in terms of being implemented as a mobile device, one of ordinary skill in the art that device 200 can be implemented in other form factors.

As shown in FIG. 2, mobile device 200 includes one or more processors, such as processor(s) 202. Processor(s) 202 may be any CPU, microprocessor, microcontroller, or computational device or circuit for executing instructions. Processor(s) are connected to a communication infrastructure 204 (e.g., a communications bus, cross-over bar, or network). Various software embodiments are described in terms of this exemplary mobile device 200. After reading this description, it will be apparent to one of ordinary skill in the art how to implement the method using mobile devices 200 that include other systems or architectures. One of ordinary skill in the art will understand that a computer, such as a desktop or laptop computer, may have a similar and/or identical architecture as that of mobile devices 200. Put another way, a computer can include some, all, or additional functional components as those of the mobile device 200 illustrated in FIG. 2.

Mobile device 200 includes a display 206 that displays graphics, video, text, and other data received from the communication infrastructure 204 (or from a frame buffer not shown) to a user (e.g., a doctor, nurse, healthcare provider, patient, or other user). Examples of such displays 206 include, but are not limited to, LCD screens, OLED display, capacitive touch screen, and a plasma display, to name a few possible displays. Mobile device 200 also includes a main memory 208, such as a RAM, and may also include a secondary memory 210. Secondary memory 210 may include a more persistent memory such as, for example, an HDD 212 and/or removable storage drive ("RSD") 214, representing a magnetic tape drive, an optical disk drive, solid state drive ("SDD"), or the like. In some embodiments, RSD 214 reads from and/or writes to a removable storage unit ("RSU") 216 in a manner that is understood by one of ordinary skill in the art. RSU 216 represents a magnetic tape, optical disk, or the like, which may be read by and written to by removable storage drive 214. As will be understood by one of ordinary skill in the art, RSU 216 may include a tangible and non-transient machine readable storage medium having stored therein computer software and/or data.

In some embodiments, secondary memory 210 may include other devices for allowing computer programs or other instructions to be loaded into mobile device 200. Such devices may include, for example, an RSU 218 and a corresponding interface RSI 120. Examples of such units 218 and interfaces 220 may include a removable memory chip (such as an EPROM, PROM), SD card and associated socket, and other removable storage units 218 and interfaces 220, which allow software and data to be transferred from the removable storage unit 218 to mobile device 200.

Mobile device 200 may also include a speaker 222, an oscillator 223, a camera 224, a light emitting diode ("LED") 125, a microphone 126, an input device 128, and a global positioning system ("GPS") module 230. Examples of input device 228 include, but are not limited to, a keyboard, buttons, a trackball, or any other interface or device through a user may input data. In some embodiment, input device 228 and display 206 are integrated into the same device. For example, display 206 and input device 228 may be touch-screen through which a user uses a finger, pen, and/or stylus to input data into mobile device 200.

Mobile device 200 also includes one or more communication interfaces 232, which allows software and data to be transferred between mobile device 200 and external devices such as, for example, sensor system 100, a computer (not shown), and other devices that may be locally or remotely connected to mobile device 200. Examples of the one or more communication interfaces 232 may include, but are not limited to, a modem, a network interface (such as an Ethernet card or wireless card), a communications port, a PCMCIA slot and card, USB port, one or more PCI Express slot and cards, or any combination thereof. The one or more communication interfaces 232 may also include a wireless interface configured for short range communication, such as NFC, Bluetooth, or other interface for communication via another wireless communication protocol.

Software and data transferred via the one or more communications interfaces 232 are in the form of signals, which may be electronic, electromagnetic, optical, or other signals capable of being received by communications interfaces 232. These signals are provided to communications interface 232 via a communications path or channel. The channel may be implemented using wire or cable, fiber optics, a telephone line, a cellular link, an RF link, or other communication channels.

As noted above, device 200 is configured to be communicatively coupled to sensor system 100. Device 200 is configured to run an application program that receives data from sensor system 100 and displays a calculated pressure and/or force signal on a display, such as display 206, to a user of the device 200 . . . . In some embodiments, processor(s) 112 executes a software library called Capsense available from Arduino (http://playground.arduino.cc/Main/CapacitiveSensor?from=Main.CapSense). The Capsense software library enables the transduction of an analog received from sensor 104 to a digital input for a wide variety of low capacitances (e.g., 75-2000 pF) with a single resistor, which functions as a frequency counter, coupled to one of the digital inputs I/O pins 122. The time it takes for a number of pulses, e.g., 30 pulses, to be sent from processor(s) 112 to sensor 104 and then be received back by processor(s) 112 is representative of a dimensionless "raw" capacitance, which corresponds to a multiple of microprocessor clock cycles.

In some embodiments, for example, the lower the capacitance, the lower the frequency of 50 percent duty cycle pulses. The dimensionless "raw" capacitance is converted into units of force or pressure by establishing a zero point and scale, which can be achieved by a measurement protocol.

Figure 3:
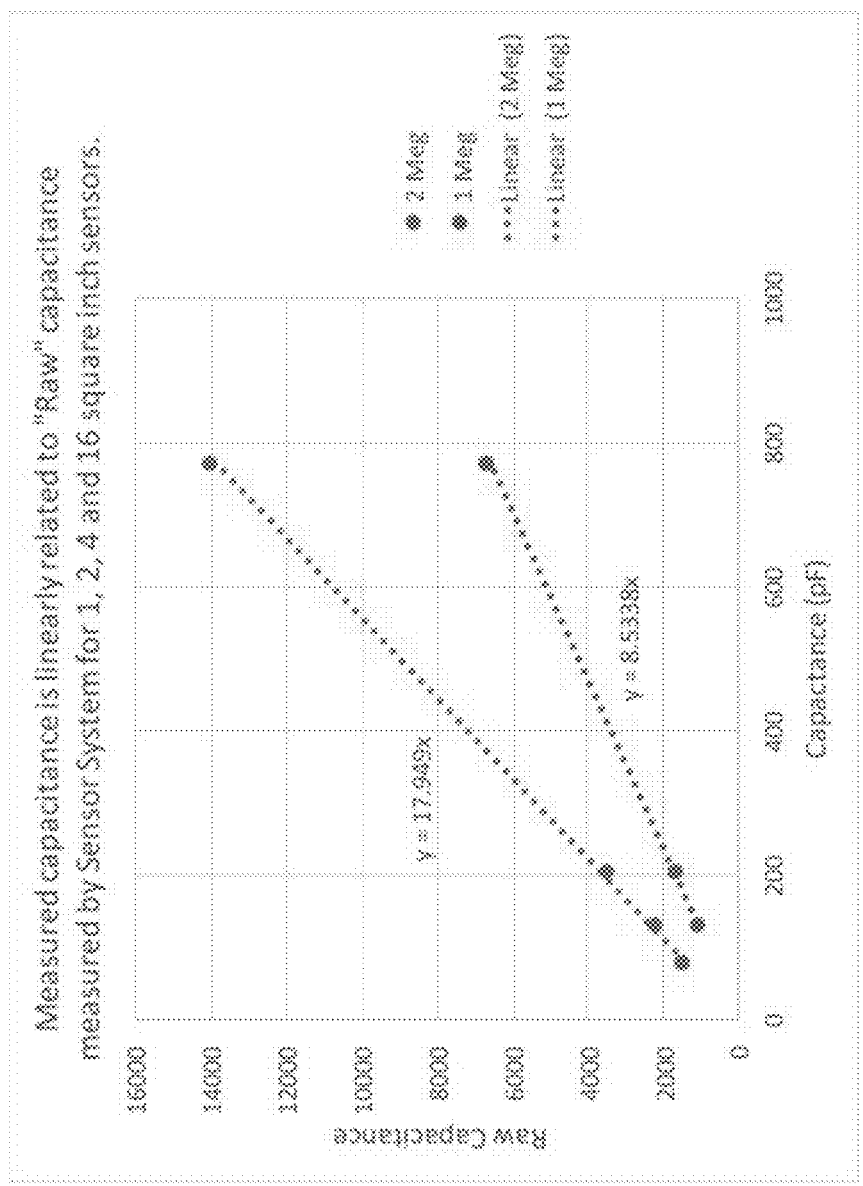
FIG. 3 is a graph of one example of a linear relationship between measured capacitance of a sensor and the raw capacitance for two values of a resistor in accordance with some embodiments.

Specifically, the force signal is calculated by processor(s) 112 of sensor system 100 is based on the product of resistance 126 and capacitance 104 as the RC time constant. The RC time constant is a function of clock cycles of the processor(s) 112. In some embodiments processor 112 is an ATmega328p microcontroller operating at 8 MHz. FIG. 3 is a graphing showing one example of the linear relationship between measured capacitance of the sensor 104, raw capacitance for two values of resistor 126: 1 MΩ and 2 MΩ. For 2 MΩ, the raw capacitance is 17.9 times the measured capacitance, and for 1 MΩ, the raw capacitance is 8.5 times the measured capacitance. The Capsense library transforms measured to raw capacitance using a set of 30, 50 percent duty cycle pulses for a total period of 5.46 ms for a 1 MΩ resistor and 100 pF capacitance. FIG. 3 shows that the raw capacitance is roughly 1000 pF. Therefore, each raw capacitance cycle is 55 microseconds, and each raw capacitance cycle is roughly 440 microprocessor clock cycles.

Figure 2A:
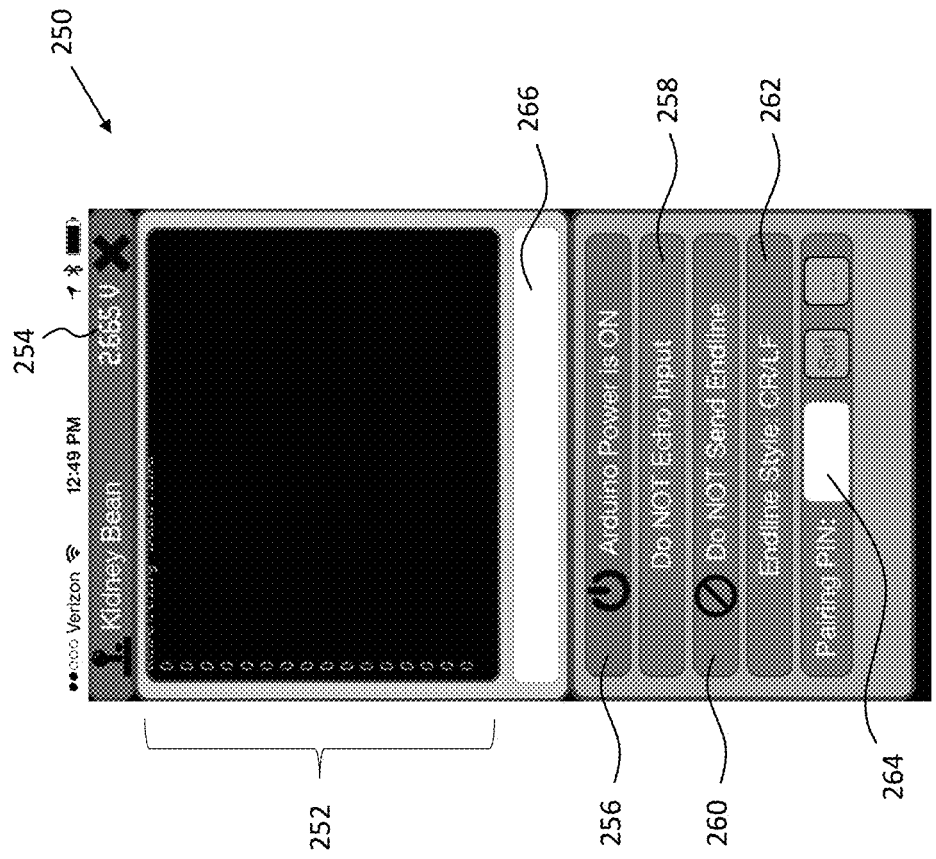
FIG. 2A illustrates one example of a graphical user interface that can be displayed to a user of a device for monitoring pressure or other forces in accordance with some embodiments.

FIG. 2A illustrates one example of a graphical user interface (GUI) 250 that may be displayed to a user on display 206 of a device 200. As shown in FIG. 2A, GUI 250 displays a serial stream of data in area 252 with each "0" corresponding to a separate force/pressure measurement obtained from a sensor system 100. GUI 250 also displays the voltage output by the power supply 124 of the sensor system 100 in area 254. GUI 250 also displays the name of the current sensor system 100 connected, in this case "Kidney Bean." GUI 250 also includes a number of buttons/user interfaces enabling a user to toggle the power of the sensor system 100 on and off by tapping area 256 and to echo the input by tapping area 258. As shown on FIG. 2A, GUI 250 is the receiver (Rx) of a serial terminal emulator. This serial terminal emulator is available on the Apple iPhone App Store as "Bean Console." For this application, serial numbers (in this case pressure data) are received by the Bluetooth communication interface 232 and displayed successively in display area 252. When numbers populate the entirety of area 252, they scroll up from the bottom. The area 266 just below the Rx area 252 is the transmitter (or Tx) line. On the Tx line 266, the operator enters a series of commands that the device 200 sends to the electronics 108 (e.g., a Bean"). In some embodiments, these commands are a set of capital letters as described in more detail below. Other elements of FIG. 2A are typical for a serial terminal emulator. For example, "echo" allows what is entered on the Tx line to appear or "echo" in the Rx area 252. Item 258 is shown in FIG. 2A as being disabled. Endline (260, 262) allows every new serial number gets a new line. In this application, endline is allowed (260). Endline style, if disabled, allows a carriage return and line feed. Item 264, if enabled, allows pairing of a Bluetooth with another device.

As described briefly above, in some embodiments, sensor system 100 and device 200 are configured to communicate with each other via a wired connection or via wireless protocol, such as by Bluetooth, NFC, WIFI, or other protocol. The processor(s) 112 of electronics module 108 and processor(s) 202 of device 202 each may execute instructions of a respective program whereby device 200 may control and/or interrogate electronics module 108 of sensory system 100. For example, in some embodiments, device 200 can turn on and/or cause electronics module 108 to begin monitoring the pressure exerted on sensor 104.

Figure 4:
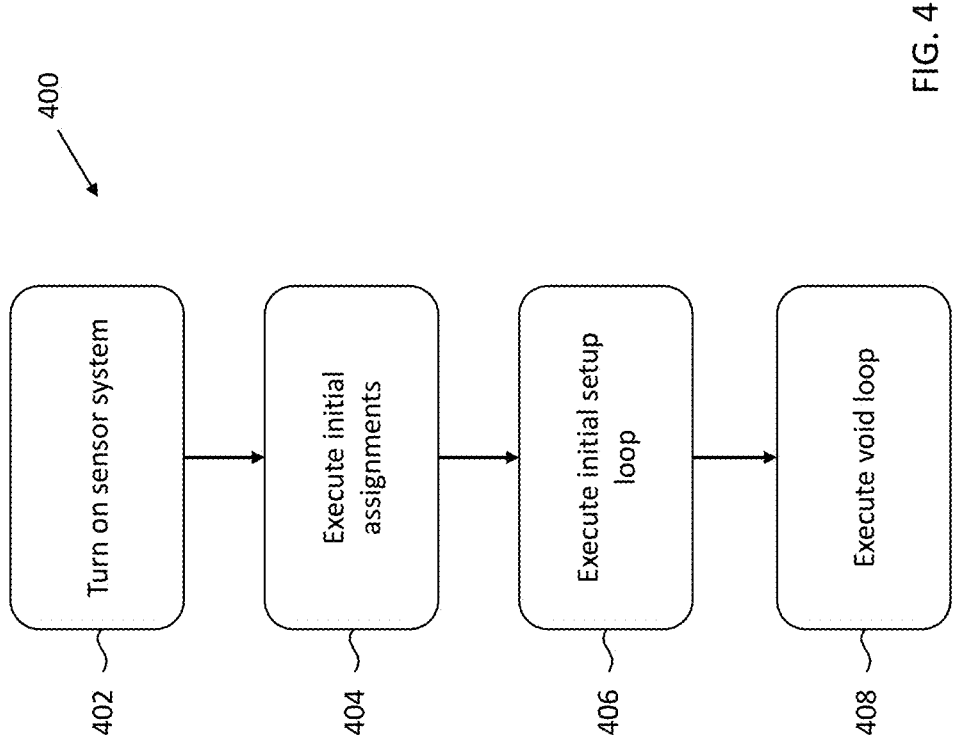
FIG. 4 is a flow diagram of one example of a calibration process in accordance with some embodiments.

FIG. 4 is a flow diagram of one example of a pressure measurement protocol 400 in accordance with some embodiments. This flow diagram summarizes functions of the program or "sketch" in C++ outlined in the Appendix. Note that the Bean can be turned on and off by remotely pressing the Arduino on/off button line 256. However, more commonly the unit will be turned on by an accelerometer interrupt that senses two taps in quick succession.

At block 402, the sensor system 100 is turned on. In some embodiments, sensor system 100 is turned on by throwing, pushing, or otherwise actuating a mechanical switch. However, in some embodiments, the sensor system 100 is turned on in response to being moved, such as by a person, or in response to receiving a signal, such as a signal transmitted from a device 200.

At block 404, initial assignments are executed. For example, in some embodiments, the initial assignments execution includes processor(s) 112 calling the Capsense software library, capacitive sensor pins are setup, and constants for rest of the "sketch" or software are established.

At block 406, an initial setup loop is executed. In some embodiments, the initial setup loop includes initializing an accelerometer to 8 g full scale and low power mode by enabling the accelerometer interrupt ("wake on connect") and setting a baseline gain and gain square (second order polynomial) obtained through a calibration routine. In some embodiments, the calibration routine includes reading an initial raw capacitance as function of pulses between I/O pins 122, such as pins 2 and 5 of the Arduino. This raw capacitance value is assessed a number of times, e.g., 10, 20, 30, 40, 50, 60, etc., and then an average is taken.

An indefinitely repeating loop ("void loop") is executed at block 408 to find a running average of raw capacitance from successive sample segments. In some embodiments, the void loop includes measuring the pressure exerted on sensor 104 and subtracting the running raw average from an initial raw capacitance to find current raw cap above baseline. If there is a reset command, the latest raw capacitance is set as the new baseline.

Figure 4A:
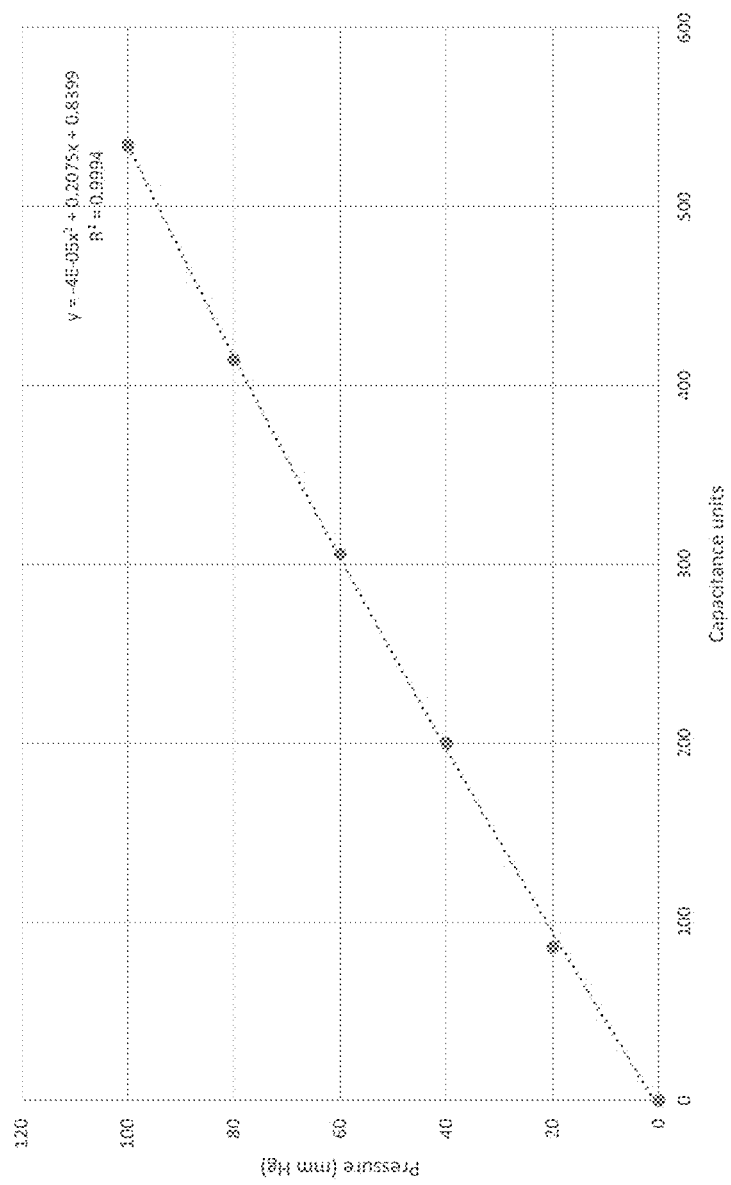
FIG. 4A illustrates one example of a linear gain versus raw capacitance change as a function of vacuum for a sensor in accordance with some embodiments.

The pressure in mm Hg is fit to a second order polynomial function of raw capacitance as shown in FIG. 4A. As shown in FIG. 4A, the second order polynomial is $y=-4e-0^{5\times 2}=0.2075x+0.8399$ where $R^2=0.9994$.

An index that automatically counts up and turns sensor system 200 "off" (sleeping and not advertising; "deep sleep") in 15 minutes (or other time period) can also be setup.

In operation, commands are received serially by electronics 108 from mobile device 200. In some embodiments, the commands are entered on the Tx line 266. For example, entering an "S" in Tx line 266 puts the electronics 108 to "sleep" (e.g., a Bean.sleep( ) command); entering an "R" in Tx line 266 causes the pressure to be reset to zero (and in the program stores the current raw capacitance as the baseline); entering a "G" in Tx line 266 causes the gain to appear in the Rx area 252; entering an "A" in Tx line 266 allows the operator to change the gain; entering a "V" in Tx line 266 displays the current program version; entering a "C" in Tx line 266 causes the raw capacitance to be displayed in the Rx area 252; and entering a "D" in Tx line 266 causes the Bean and sensor combination to go to sleep and disable Bluetooth advertising.

Advantageously, the disclosed system 100 includes a low power design. For example, in normal operation, electronics 108, which can include a Bean and Bluetooth module as discussed elsewhere herein, uses about 5.0 mA. In normal operating mode, there is a constant drain of 4 mA and a 3 ms pulse of 10 mA every 27 ms. The latter is the Bluetooth low energy advertising signal. Advertising is an announcement that lets Bluetooth receivers, know that the sensor system 100 is available. With a lithium battery CR2032 there is an effective capacity of 150 mA-hours. Therefore, if left on the battery will expire in approximately 30 hours.

In some embodiments, the battery life the electronics 108 can be increased. For example, the Bean can go into "sleep mode" which brings down current drain down to 125 μA. This includes very low current drain of <50 μA, plus a short advertising signal (3 ms, 21 mA, occurring every 497 ms). In order to increase battery life further, the Arduino processer can be put into "deep sleep". Advertising is disabled and battery drain is about 75 μA. If not used, the device in deep sleep could last as long as 3 months.

When configured not to advertise, the sensor system 100 can be awoken from a "deep sleep" via a mechanical stimulus. For example, an accelerometer interrupt can be configured to sense a double tap causing it to "wake up" the Bean and it resume advertising and cycling again through the "void loop". In some embodiments, a "pin change" interrupt can be implemented in which the electronics 108 are woken up by an external motion switching being thrown or otherwise actuated. Once turned on, an index automatically induces "deep sleep" again in 15 minutes. This index resets to zero if there is any activity (greater than 10 mm Hg change) on the capacitive sensor 104.

In some embodiments, the calibration can be set for a specific sensor type and dimension using a pressure/vacuum chamber. For example, the sensor can be placed in a pressure/vacuum chamber and the output of the sensor system is compared to the known condition. FIG. 4A is a pressure versus capacitance graph of a sensor being calibrated in a small pressure chamber against a "standard" pressure monitor between 0 and 100 mm Hg. The particular sensor used to obtain the data in FIG. 4A was formed from type 30 (soft) Poron that was 0.035 inches (0.889 mm) thick, folded three times as per FIG. 1B, measured 1 inch by 4 inches. A second order trend line in FIG. 4A reveals the first and second order calibration constants: second order $-4*10-5$ and first order 0.275. These first and second order calibration constants are then programmed into the setup loop. Alternatively, they might be entered by an "A" command on the Tx line 266 and typing in the new coefficients when prompted.

Figure 4B:
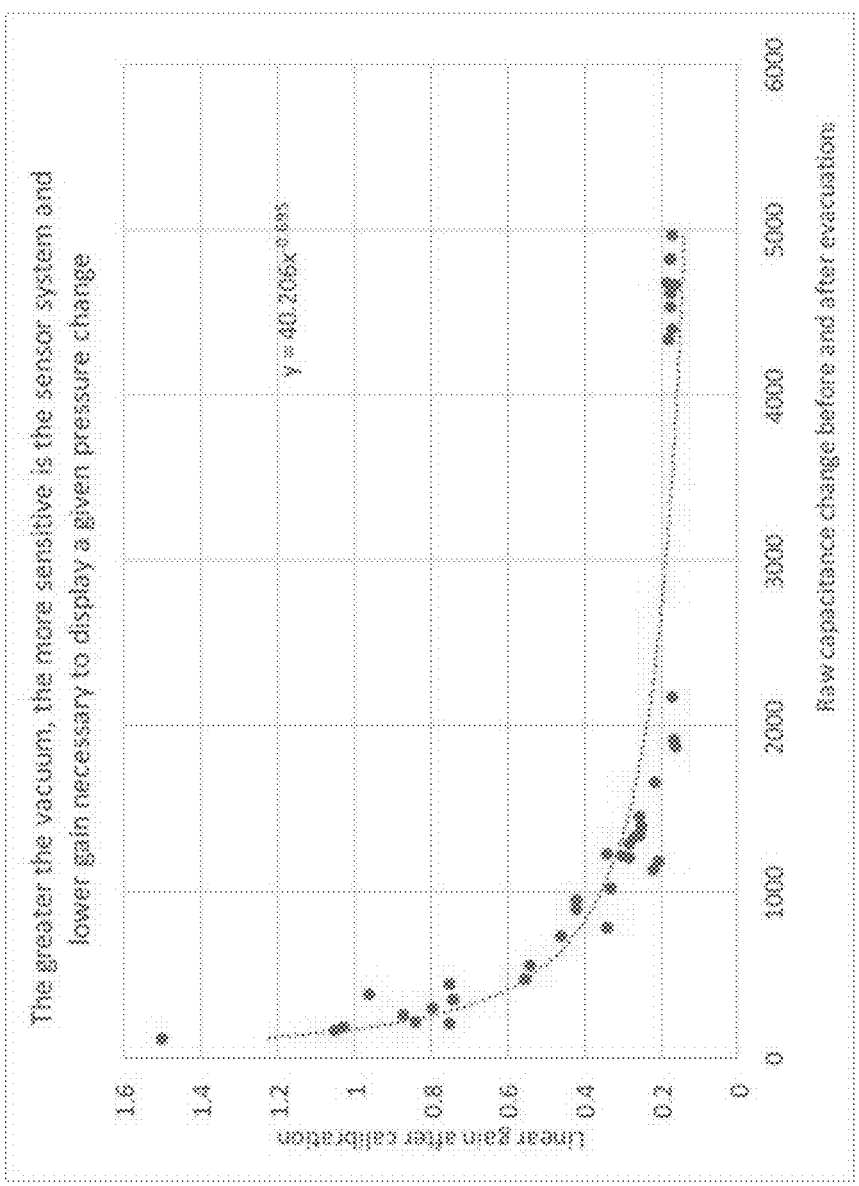
FIG. 4B illustrates one example of a pressure versus capacitance units graph for a sensor in accordance with some embodiments.

One novel characteristic of this capacitive sensor prepared in a vacuum is that the linear gain is predictable and stable, which is confirmed by calibration. For instance, over a broad range from 10 to 13.5 PSI vacuum sensitivity is high and gain is low and constant. This is demonstrated in FIG. 4B which is a plot of linear gain versus raw capacitance change before and after vacuum is applied. An empiric power function is apparent and a minimum gain of 0.2 over a wide range of higher vacuum conditions.

Figure 4C:
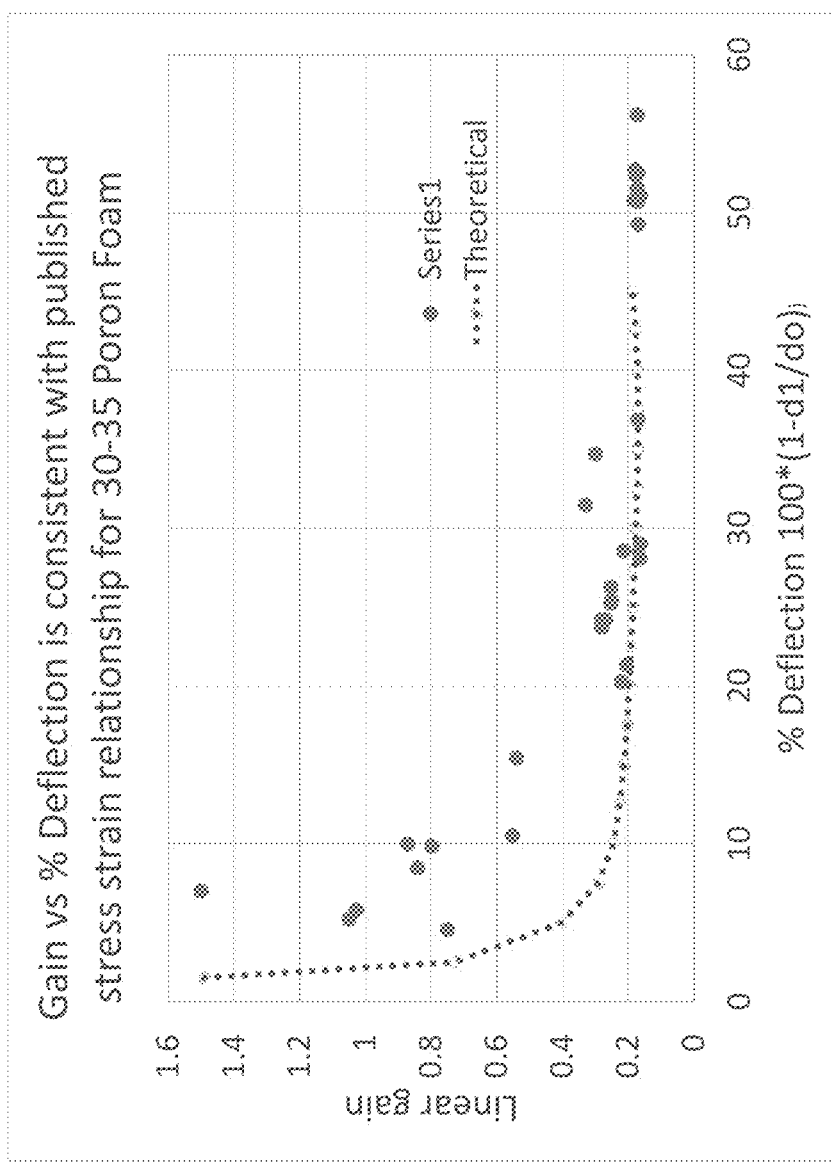
FIG. 4C illustrates one example of a graph comparing gain versus percent deflection for both theoretical calculations and actual measurements in accordance with some embodiments.

The sensor system independently confirms manufactures stress-strain specifications. To confirm this, FIG. 1C is modified by transforming the y-axis from pressure (PSI) to gain and plotted against percent deflection in the manner of FIG. 1C. The stress-strain relationship for Poron foam has three phases: 1) less sensitive and stiffer initial cell collapse phase; 2) more linear mid-range collapse phase; and 3) less sensitive more stiff "bottoming out" phase. Raw capacitance change is a measure of loss of foam thickness or percent deflection $(1-d/do)*100$. In a partial vacuum of negative pressure 13.5 PSI, ambient pressure subjects the sensor to equal positive pressure of the same amount. This causes the greatest deflection of the foam and capacitance increase. In FIG. 1C this is 45% deflection for 30-35 Poron foam. A lower vacuum will flatten or deflect the foam less, causing less capacitance increase. This can condition can be referred to as creating a steady state vacuum "bias". Around this bias there will be more or less slope of the pressure deflection curve for a given percent deflection. The inverse is also true. For example, there will be more or less slope of the percent deflection versus pressure curve depending on the location on the pressure curve. If there is more deflection change at a given pressure (or vacuum) the sensor is more sensitive. Also, lower gain would be required to achieve a calibrated pressure. Therefore, more deflection leads to higher more stable sensitivity and constant, low gain even if the housing 102 loses considerable pressure. This is shown in FIG. 4C. For FIG. 4C, the horizontal axis is derived as follows:

First, deflection is calculated as $(1-d1/d0)$, where d1 is the deflection with pressure applied, and d0 is the condition without deflection. As will be understood by one of ordinary skill in the art, capacitance can be determined by the equation C=k (A/d), where k is the dielectric constant of a material, A is the area of a capacitor plate, and d is the distance between the capacitor plates. If C0 is the raw capacitance before evacuation and C1 is the raw capacitance after calibration, then C0/C1=d1/d0, where C0/C1 is the ratio of raw capacitance before and after vacuum is applied. Therefore, percent deflection (% Deflection in FIG. 4C) may be given as the following equation:

% Deflection=100*(1−C0/C1)   (Eq. 1)

The vertical axis of FIG. 4C is gain, which is the linear gain of a particular sensor empirically measured from calibration for 0 to 100 mm Hg. The gain is the change in unit pressure (calibrated in mm Hg) at a given pressure "bias" on the sensor. For FIG. 4C, the theoretical relationship between gain and % Deflection closely follows the manufacturer's published stress-strain relationship published by Rogers group for 30-35 Poron (shown FIG. 1C).

For example, the stress strain relationship for 30-35 Poron is inverted to a graph of % Deflection (described below) on the vertical axis and pressure on the horizontal. Pressure is converted from PSI to mm Hg. This function of deflection vs pressure in PSI fits the following third order polynomial within 10%:

$y = -1e{-07}x^3 + 0.0002x^2 - 0.0158x + 0.5804$   (Eq. 2)

The sensitivity can be determined by taking the differential of Eq. 2, which yields:

$d(\% \text{ Deflection}0)/d(\text{pressure}) = -3E{-07}x2 + 0.0004x - 0.0158$, where $x$ is % deflection   (Eq. 3)

Sensitivity, S, is inversely proportional to gain according to:

$S(o)/S1 = \text{gain}1/\text{gain}(o)$, OR $T = S(o)*\text{gain}(o)$.

S(o) and gain(o) are experimentally obtained. Therefore, the following is true gain(1)=T/S(1).

Theoretical gain derived from the above steps is plotted versus % Deflection as the hatched line on FIG. 4C. The hyperbolic curve shape fits empirical measurement with certain limitations. The experimental curve shifts 7.5% to the right of the theoretical one. This might be due decreased sensitivity of the sensor especially at lower vacuum. Above 10 PSI a 5 mil think PE/nylon laminate sheet was used, 0.01 inches (0.254 mm) for both sides. However, below 10 PSI the inventor used a Foodsaver slot vacuum system with multiple layers of nylon/low density polyethelene, 0.0115 inches (0.2921 mm) thick with texturing on one side and 0.003 inches (0.0762 mm) on the other). The extra thickness and texturing might have decreased sensitivity at lower pressures, more than what would be predicted.

Alternatively, the shift to the right might be due to small proportion (potentially up to 5%) of the foam not compressing in the vacuum due to the presence of folds. If the area compressed at is 90% that at 0% deflection, raw capacitance Co/C(1) increases apparent deflection by a factor of 1.05. This will have the effect of shifting the theoretical curve toward the right.

The foregoing discussion is intended to illustrate how vacuum improves the sensitivity and stability of the foam as a capacitive sensor. It also helps to illustrate how this novel use of vacuum takes full advantage of the second phase of the stress-strain characteristic of open cell foam. It also demonstrates how physical design of the sensor causes slight deviations from predicted.

As will be understood by one of ordinary skill in the art, the housing 102 can experience a slow reduction in the vacuum over time depending on the material used for housing 102. For example, it has been estimated that a polyethylene/nylon laminate bag will experience a reduction in vacuum of approximate 3.5 percent per week. The stable gain over a range of vacuum from 10-13.5 PSI means that the sensor 104 will retain its performance for an extended period of 10 weeks. If Mylar with a thickness 0.0043 inches (0.10922 mm) or 0.007 inches (0.1778 mm) is used for the material of housing 102, however, then there is no detectable decrease in vacuum per week, sensitivity and gain could be maintained for >1 year.

The capacitance of the sensor 104 can be varied based upon a variety of factors including, but not limited to, the type of dielectric material, the size of the dielectric material, and the number of layers of dielectric material used in a sensor 104. For example, for a sensor comprising five 30 mil layers of type 35 (soft) PORON®, a one square inch sensor has a capacitance of approximately 100 pF (uncompressed), a 2.25 square in sensor has a capacitance of approximately 200 pF (uncompressed), a 4 square inch sensor has a capacitance of approximately 400 pF, a 16-inch square sensor has a capacitance of approximately 1000 pF.

Manufacturing

With reference to FIGS. 5A-5Z, one example of a method of manufacturing a sensor system 100 is described. One of ordinary skill in the art will appreciate that the following description is merely exemplary and that sensor systems can be manufactured through other processes.

FIG. 5A shows a number of templates 502 being laid out on a sheet of metallizing fabric 504 available from Swift Textile Metalizing LLC of Bloomfield, Conn. In the example shown in FIG. 5A, the pattern is for a 2.25 square sensor and the fabric 504 has been placed on a piece of cardboard to which a 3M contact adhesive had been applied in a "tacky" stage. The fabric 504 is stretched to remove any wrinkles in order to provide a smooth surface. FIG. 5B illustrates the patterns having been cut into two types of sections 505, 506. Sections 505-1, 505-2, 505-3, 505-4 (individually "section 505"; collectively "sections 505") each includes two 2.25 squares, and sections 506-1, 506-2, 506-3, 506-4 (individually "section 506"; collectively "sections 506") each includes four 2.25 inch square.

Figure 5D:
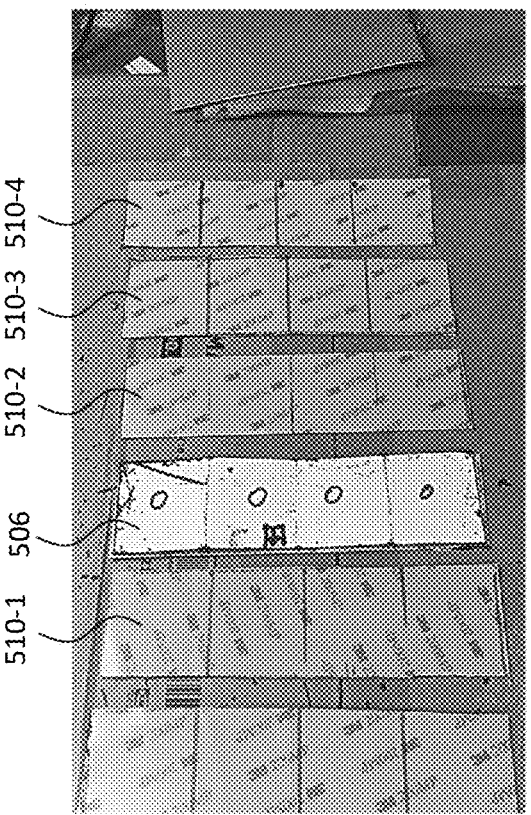
FIGS. 5A-5R illustrate a sensor system at various points of manufacture in accordance with some embodiments.
Figure 5C:
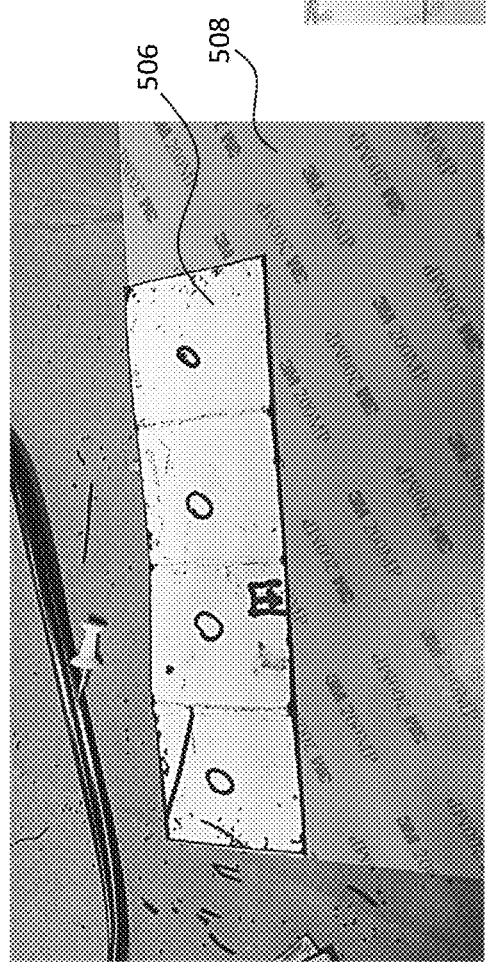

FIG. 5C illustrates a pattern section 506 being placed on a sheet 508 of dielectric foam (e.g., type 35 (soft) PORON®) that had adhesive (e.g., 3M 200 MP transfer tape) applied to both sides, i.e., the inside "I" and the outside "O." FIG. 5D illustrates the sheet 508 having been cut into segments 510-1, 510-2, 510-3, 510-4 (individually "segment 510"; collectively "segments 510"), with each segment 510 comprising a layer of dielectric foam with an adhesive applied to both sides. FIG. 5E illustrates a dielectric segment 510 with the outer layer 512 of the adhesive transfer tape having been removed and placed adjacent to the segment 510.

Figure 5F:
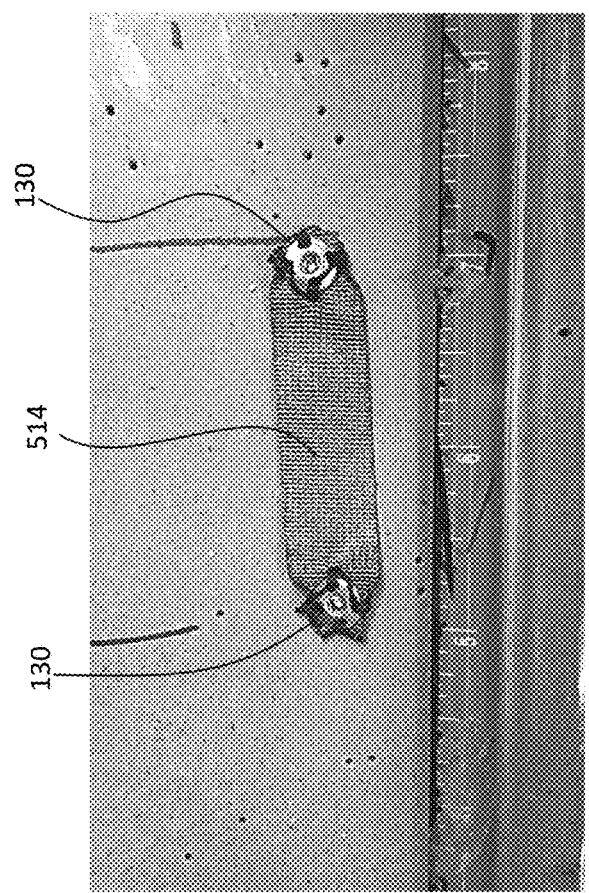
Figure 5E:
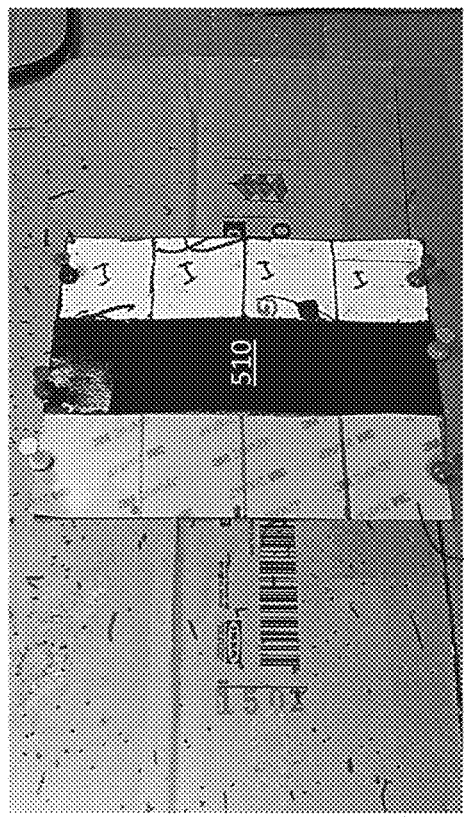

FIG. 5F illustrates a pair of mechanical and electrical fasteners 130, which in this embodiment is shown as a pair of snaps, being coupled to a layer of metalized fabric 514 that is coated with a conductive contact adhesive and a layer of conductive carbon. In some embodiments, the metalized fabric 514 is the same fabric as fabric 504. Mechanical and electrical fasteners 130 are shown in FIG. 5F as being coupled to fabric 514 by sewing, however, one of ordinary skill in the art will understand that other means of attachment or coupling can be used. FIG. 5G shows the metalized fabric 514 having been cut to provide two separate coupling assemblies 516-1 and 516-2 with each assembly 516 including a mechanical and electrical fastener 130 coupled to a metalized fabric 514.

Figure 5H:
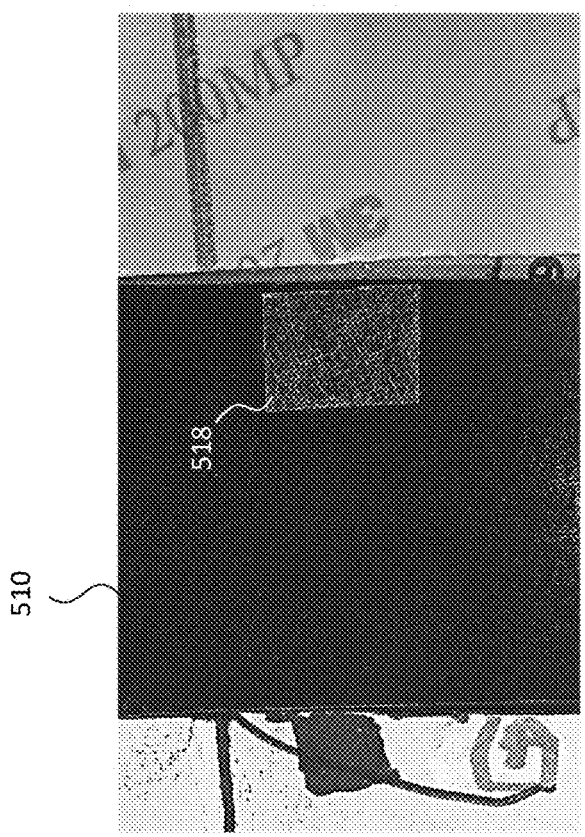
Figure 5G:
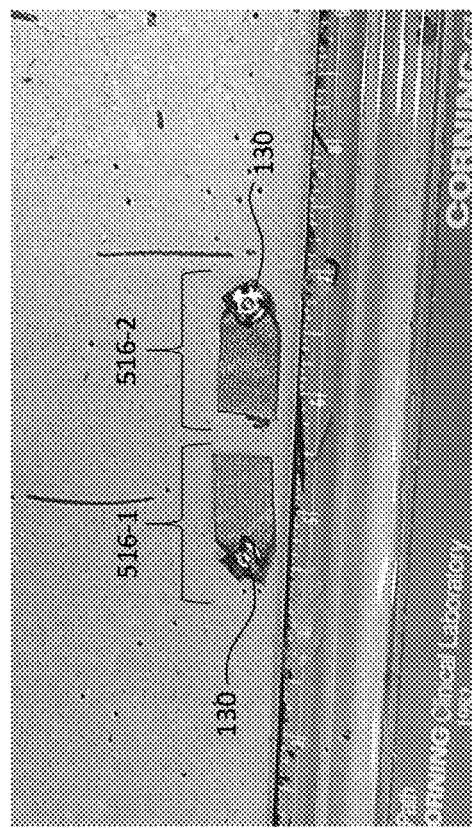

FIG. 5H shows a conductive adhesive 518 being applied to one side of the segments 510 of dielectric foam. One example of a conductive adhesive is the 9719 XYZ electrically conductive tape available from the 3M Company of Maplewood, Minn. The application of the conductive adhesive 518 to dielectric foam segment 510 increases the electrical connection of the coupling assemblies 516 to foam segment 510. Although a conductive adhesive 518 is shown being coupled to only one side of the foam segment 510, one of ordinary skill in the art will understand that the conductive adhesive 518 can be coupled to both sides of segment 510.

Figure 5J:
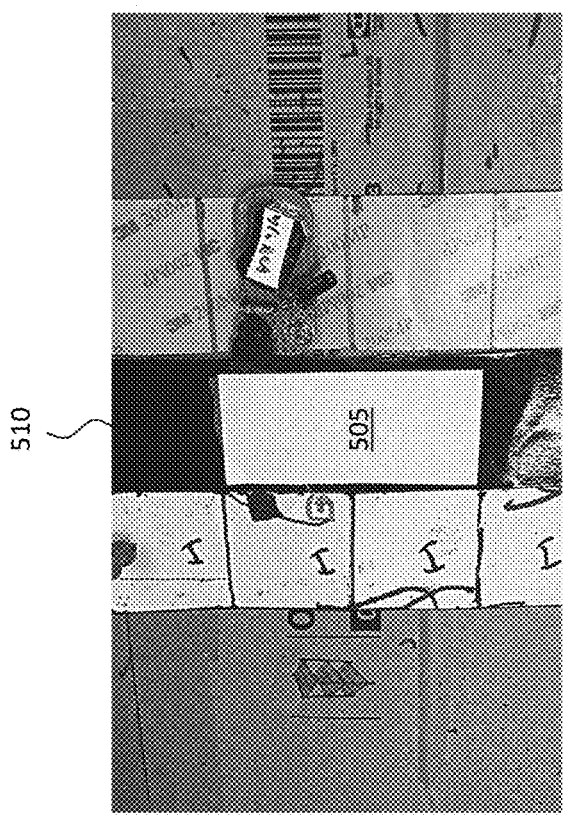
Figure 5I:
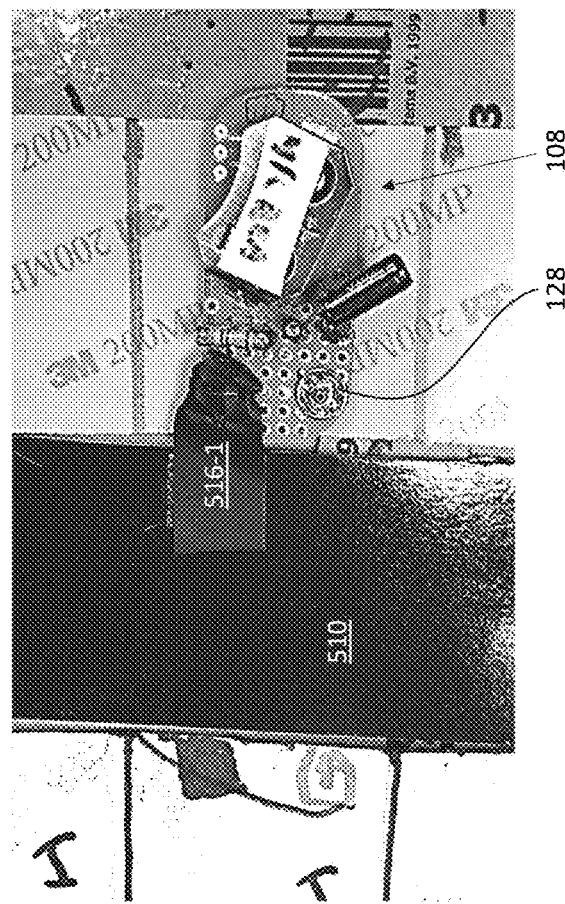

FIG. 5I illustrates a coupling assembly 516 that is coupled to dielectric foam segment by way of conductive adhesive 518 (not shown). Also shown in FIG. 5I are the electronics 108 with one mechanical and electrical fastener 128 being coupled to the mechanical and electrical fastener 130 of the coupling assembly 516-1. With coupling assembly 516-1 secured to foam segment 510, a section of a two-panel metallized fabric 505 (i.e., a section including two 2.25-inch squares) is applied over the dielectric material segment 510 and over a portion of the coupling assembly 516-1 as shown in FIG. 5J. Note that a protective sheet is covering the two-panel metallized fabric section 505 in FIG. 5J.

Figure 5L:
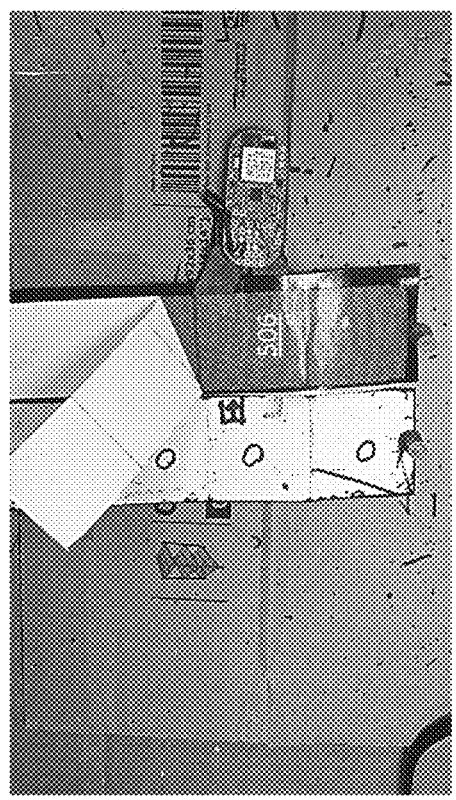
Figure 5K:
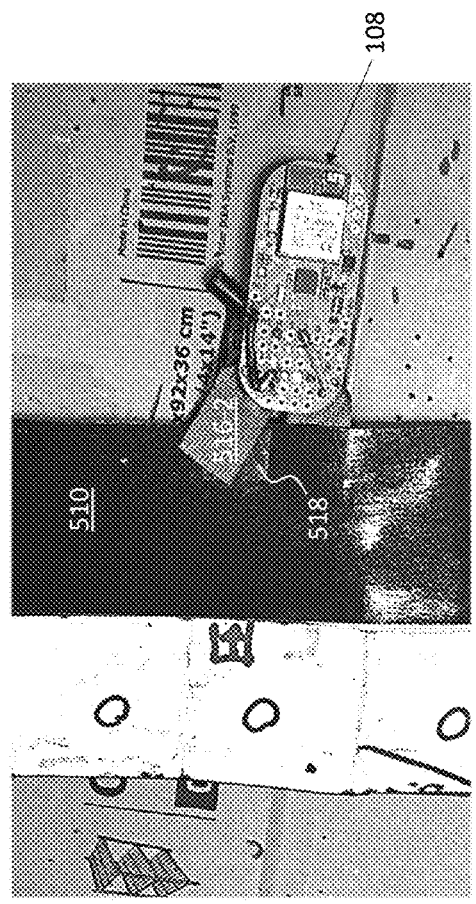

The assemblage shown in FIG. 5J is then flipped over such that the other coupling assembly 516-2 can be coupled to the outer side "O" of segment 510. FIG. 5K illustrates a coupling assembly 516-2 being applied to a conductive adhesive 518 that is secured to segment 510. With coupling assembly 516-2 secured to conductive adhesive 518 on the outside "O" of segment 510, a four-panel metallized fabric segment 506 is secured to the outer side "O" of segment 510 as shown in FIG. 5L. Note that FIG. 5L also shows a protective sheet being peeled off of the four-panel metallized fabric segment 506.

Figure 5N:
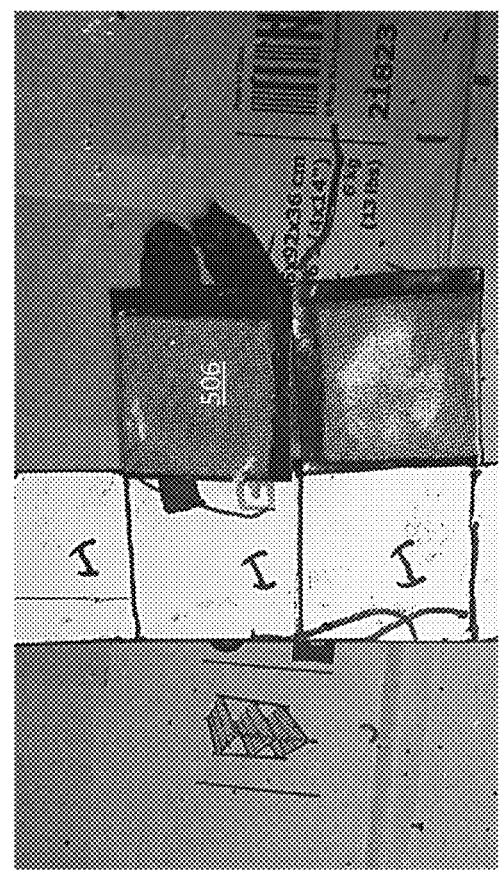
Figure 5M:
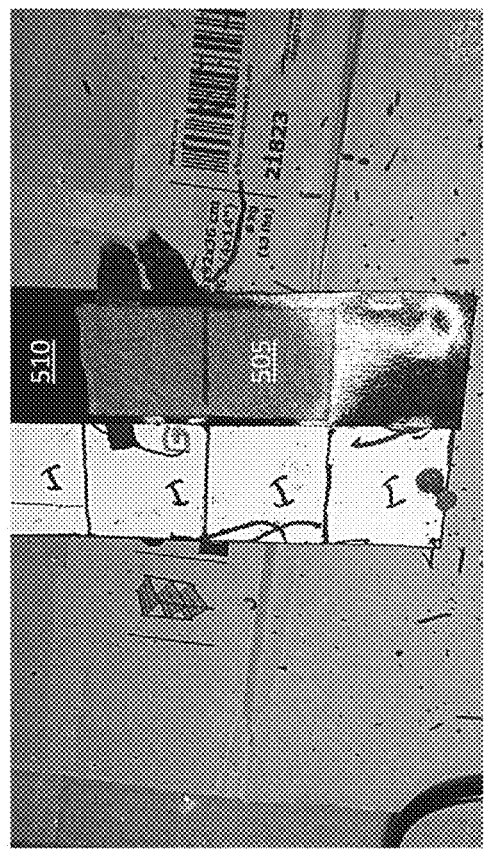

The assemblage shown in FIG. 5L is then flipped over again such that inner side "I" with the two-panel metallized fabric 505 is face up and the outer side "O" with the four-panel metallized fabric 506 faces the work surface. This arrangement is shown in FIG. 5M with the protective sheet having been peeled off of two-panel metallized fabric 505. As best seen in FIG. 5N, the segment 510 is folded such that the two-panel metallized fabric segment 505 is covered and located in the interior of the resultant sensor. The two panels of the metallized fabric visible in FIG. 5N are two of the four panels of fabric 506.

The assemblage is folded again such that the two panels of fabric 506 seen in FIG. 5N are placed in contact with one another. A conductive adhesive 518 can be placed between these two panels prior to folding to help secure these panels to each other. The resultant multi-layer sensor structure 104 is shown in FIG. 5O.

The electronics 108 are then attached to the sensor 108 using the mechanical and electrical fasteners 128 and 130. As shown in FIG. 5P, the electronics 108 are wrapped in a protective wrap 520 for cosmesis, protection, and to prevent leaks in the vacuum. In some embodiments, the protective wrap 520 includes a layer of non-sleep material available from the Dycem Corporation of Warwick, R.I. FIG. 5P also illustrates an angled section 522 of the protective wrap 520 having been removed to provide a window for an LED of the electronics that identifies that the electronics 108 are powered on or off.

Figure 5R:
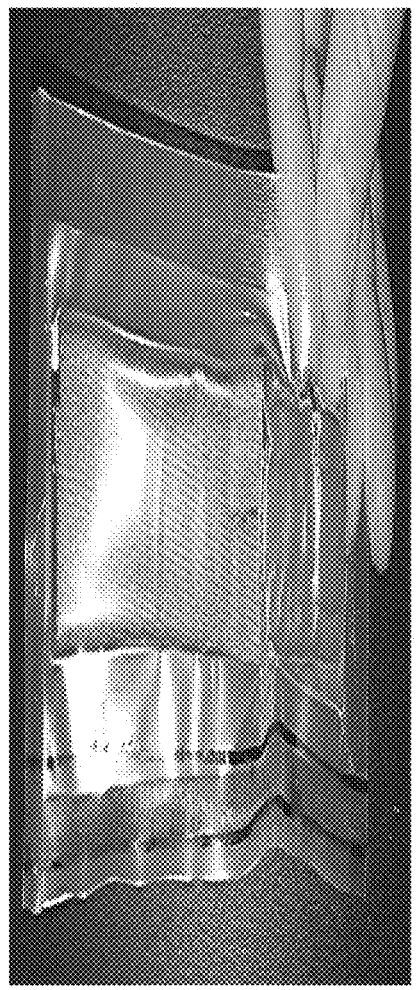
Figure 5Q:

The sensor 104 and electronics 108 are then placed together in a housing 102 as shown in FIG. 5Q. As described above, housing 102 can be in the form of a sealable bag formed from polyethylene, Mylar, or other sealable and relatively gas-impermeable membrane or material. A vacuum is then created within the housing 102 and the vacuum is then sealed. In some embodiments, the vacuum within housing 102 is approximately 13.5 PSI, although one of ordinary skill in the art will understand that other pressures can be provided within housing 10, and the seal is provided by an impulse sealer. FIG. 5R illustrates one example of a sensor system 100.

Clinical Applications

The sensors and sensor systems described herein can be used in a wide-variety of clinical applications. The following discussion of examples should not be considered to be limiting as the sensor systems discussed herein can be deployed in additional applications beyond those discussed herein.

I. Sub-Bandage/Cast

Figure 6:
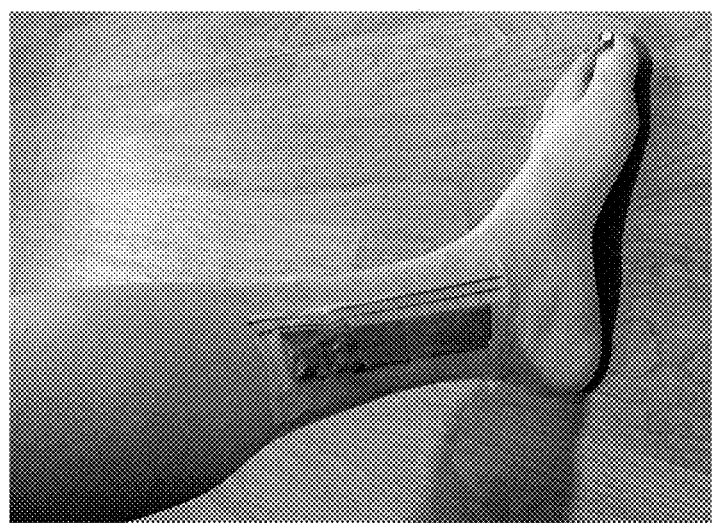
FIG. 6 illustrates one example of a sensor system being used to monitor the pressure exerted on a patient by a self-adhesive wrap in accordance with some embodiments.

In some embodiments a sensor system is wearable and positioned against a person's skin within a bandage. FIG. 6 illustrates one example of a sensor system 100-2 being positioned on a calf of a patient. More particularly, the sensor system 100-2 is placed at the medial ankle between the hell and malleolus. A bandage (not shown in FIG. 6), such as a self-adherent bandage (e.g., Coban wrap), can be wrapped around the sensor system 100-2. In such applications, the pressure sensed by the sensor system 100-2 follows a slow oscillating pattern based on "ankle pump" as the ankle pumps up (dorsiflexes) and down (plantarflexes). The pressure on the sensor system 100-2 increases during dorsiflexion and decreases during plantarflexion.

Figure 7A:
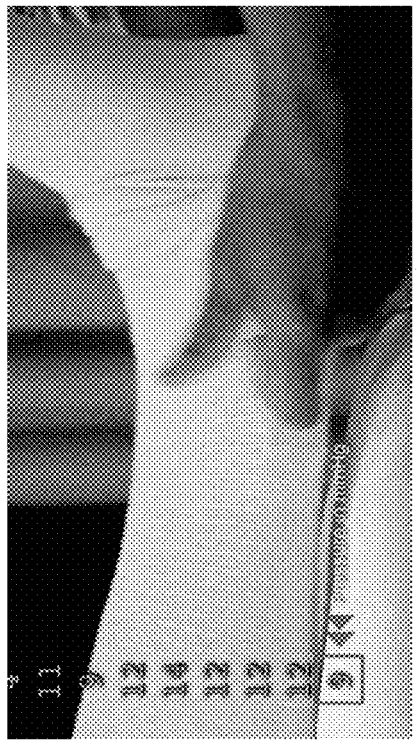
FIGS. 7A and 7B illustrate one example of a sensor system for use in monitoring the pressure exerted on a patient by a tubular wrap in accordance with some embodiments.
Figure 7B:
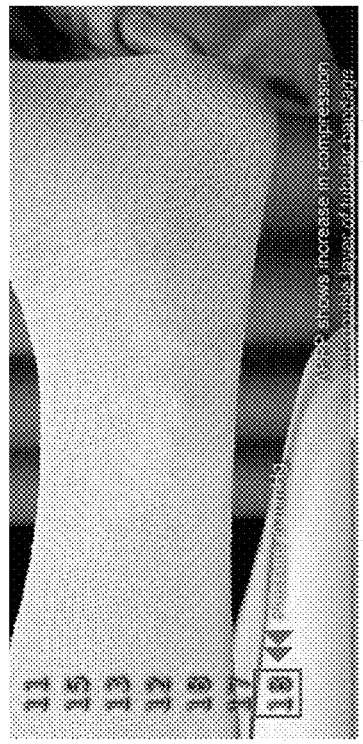

FIGS. 7A and 7B illustrate a pair of bandages being applied to a patient over a sensor system, which is not visible in these figures. FIG. 7A shows that as a first tubular bandage, such as a Tubigrip, is applied, the bandage exerts approximately 9 mm Hg of pressure. The pressure increases to 18 mm Hg when the second tubular bandage is applied as can be seen in FIG. 7B.

In addition to soft bandages, such as the self-adherent and tubular bandages discussed above, a sensor system can also be used to monitor the pressure within a cast. In such embodiments, the sensor 104 is placed within the cast and the electronics 108 can be placed outside of the cast with electrical connection between the sensor 104 and electronics 108 being provided by a segment of the same sensor 102. Sensor systems disposed between the patient and cast can be used to assess the success of limited weight bearing under a diabetic foot ulcer.

Figure 8B:
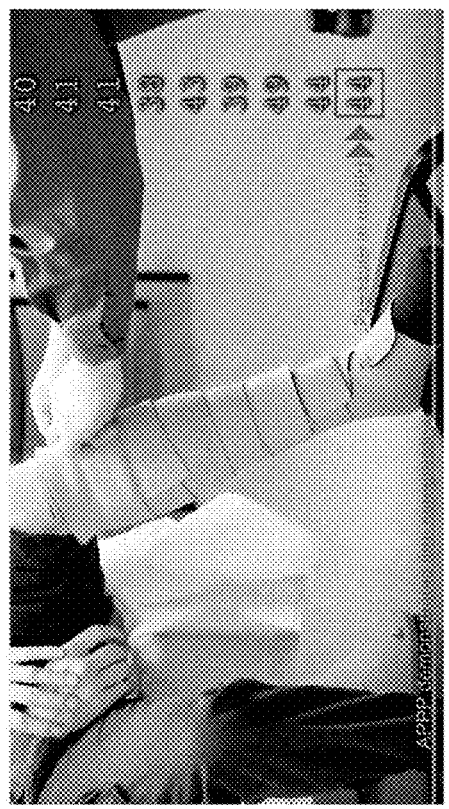
FIGS. 8A and 8B illustrate one example of a sensor system being used to monitor lymphedema as compression straps are being applied in accordance with some embodiments.
Figure 8A:
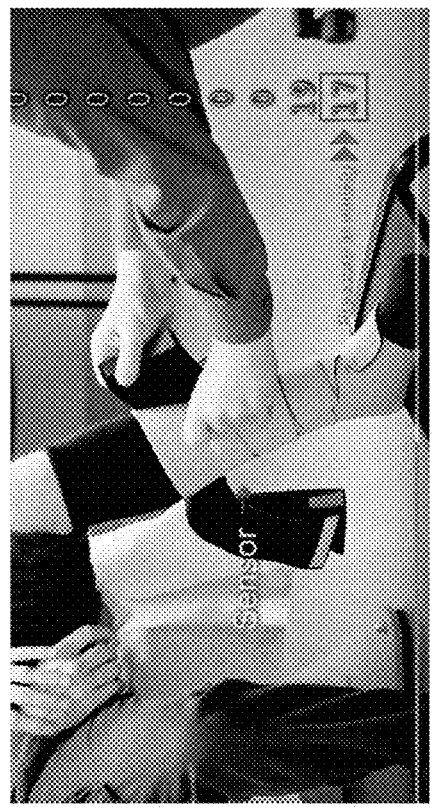

FIGS. 8A and 8B illustrate a sensor system being used in connection with the treatment of lymphedema. Long term lymphedema treatment involves use of garments with horizontal straps with hook and loop closures that provide compression (Farrow Wraps, Solaris, Circ-aide). For example, FIG. 8A shows compressive straps being applied to a patient. The sensor system (not shown) has electronics 108 slipped within a pocket over the posterior leg which are part of the garment itself. The sensor in FIG. 8A is placed posteriorly at the mid leg. As straps are tightened over the mid leg, the measured pressure, as communicated from the sensing system to a remote device, is 17 mm Hg. As more proximal straps are tightened, pressure at the mid leg increases to 44 mm Hg (FIG. 8B) as read from the remote device 200. In the application shown in FIGS. 8A and 8B, a sensor system having a 2.25 square inch sensor was used and applied to the patient at the level of mid-leg posteriorly.

As seen in FIG. 8B, as more straps are overlapped and secured there is a cumulative increase in pressure sensed by the sensing system.

II. Training Sensor

Figure 9:
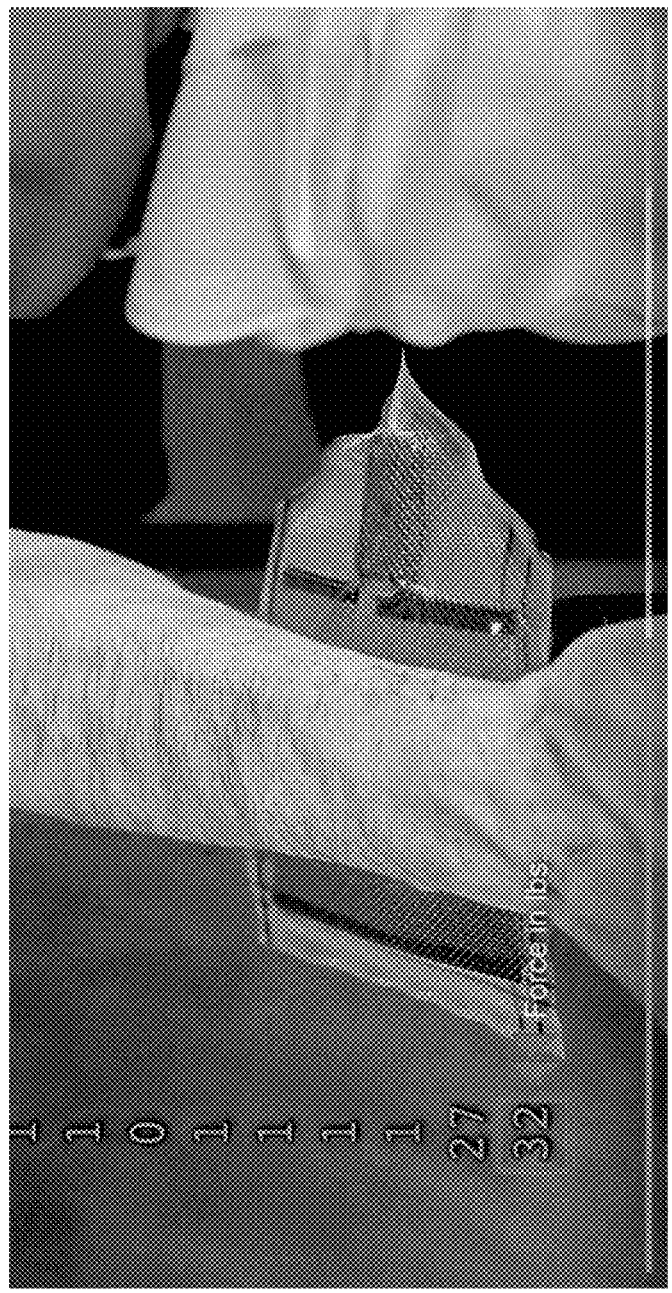
FIG. 9 illustrates a sensor system being used as an isometric exerciser or manual muscle tester for training and measuring across multiple joints in accordance with some embodiments.

Sensing systems can also be used to monitor exercises and workouts. For example, FIG. 9 illustrates a sensor system being used as an isometric exerciser or manual muscle tester for training and measuring across multiple joints. In the embodiment shown in FIG. 9, the sensor had a square shape with length and width dimensions of 16 inches and is used to measure the force of a patient extending his triceps. As shown in FIG. 9, a pressure of 32 pounds is measured by the sensor system, which transmits the measured force to a device 200.

The sensor system can be placed on an arm rest, desk, held by a physician or individual, or otherwise positioned or maintained against the patient's arm as the patient exerts a force on the sensor system. It should be understood that any large muscle group can be measured such as, for example, quadriceps, hamstrings, and biceps, to list only a few possible muscle groups.

III. Wheelchair Sensor

Figure 10A:
FIGS. 10A-10C illustrate a sensor system being used to monitor a stationary patient in accordance with some embodiments.
Figure 10C:
Figure 10B:
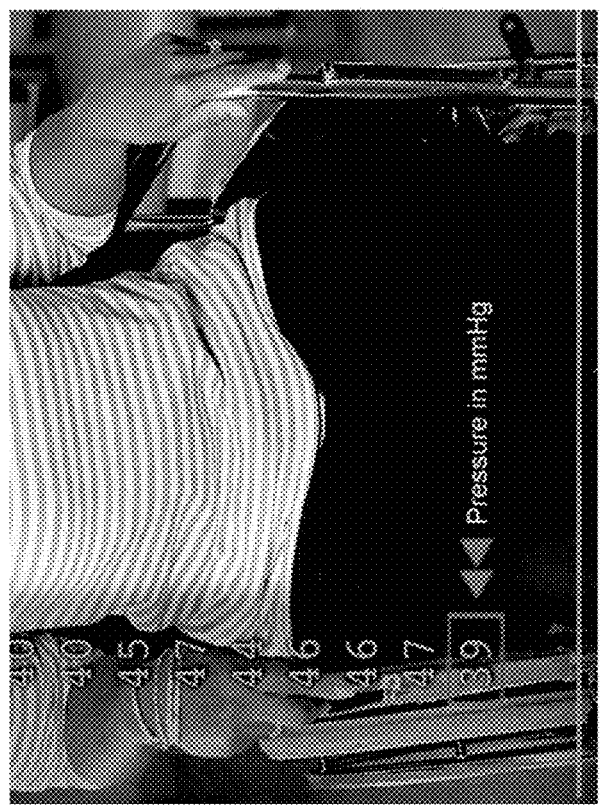

The disclosed sensor systems also can be used to monitor and/or measure the pressure certain areas of a patient experience while sitting. For example, FIGS. 10A-10C illustrate a sensor system 100-3 for being used to be placed on a wheelchair, chair, bed, or other surface on which a patient may be placed. In the embodiment shown in FIG. 10A, the sensor 104 was square in shape with the length and width both measuring 16 inches. When placed underneath the patient, the sensor system measures the pressure under the patient. Monitoring of such pressure can be used to prevent pressure ulcers and to evaluate cushions for comfort, for example.

FIG. 10B illustrates a patient sitting in a wheelchair with a sensor system located under the patient's left buttocks, which is at right in the figure. As can be seen in FIG. 10B, the patient is sitting upright in the wheelchair and thereby exerts a pressure between 39-47 mm Hg as measured by the sensor system 100-3 and output to a device 200. A seated person normally will shift to the left and right in order to maintain adequate perfusion of blood through the skin. FIG. 10C shows that when the patient shifts weight to the left buttocks that the pressure increases to 120 mm Hg. The usual amount of skin pressure that people can maintain indefinitely without pressure ulceration is about 35 mm Hg, and therefore a sustained pressure of 120 mm Hg could pose health issues to the patient.

The electronics 108 of the sensor system 100-3 or the program executed by device 200 can monitor the measured pressure over a period of time and can trigger an alert to a care giver or other person. The period of time can be configurable to a few seconds to several minutes or even hours. In some embodiments, whether an alert is generated is a function of both time and pressure. For example, an alert can be triggered if an average pressure for a period of time is above a threshold. An series of time and pressure thresholds can be provided for alert triggering. For example, the amount of time a pressure is sustained may be shorter for higher pressures than it would be for shorter pressures.

The type of alert that is generated also can be configurable. For example, device 200 can generate an audible alarm from a speaker 222 (FIG. 2), a vibration output by oscillator 223 (FIG. 2), the flashing of a light from LED 225 (FIG. 2), or the sending of an electronic message sent by SMS, email, or other means that is transmitted over a network by way of a communication interface 232.

IV. Limb Load Sensor

Figure 11A:
FIGS. 11A-11C illustrate a sensor system being used to monitor the pressure on a limb of a patient in accordance with some embodiments.
Figure 11C:
Figure 11B:

The sensor systems disclosed herein can be used to monitor the pressure on a limb of a patient. For example, FIGS. 11A-11C illustrate a sensor system being used to monitor the pressure on a foot or feet of a patient. In such embodiments, the sensor 104 is formed to have a shape that coincides to the shape of a shoe or foot of a patient such that the sensor can be inserted into a shoe or sneaker as shown in FIG. 11A. The electronics 108 can hang out of the back, side, or front of the shoe while still being coupled to the sensor 104.

FIG. 11B shows a digital readout that is presented to a user on a display of a device 200 (not shown) as the patient walks in the shoes in which the sensor system is located. As shown in FIG. 11B, the device can present serial digital output stream to a user of a device 200 as is evident in the numbers along the right of FIG. 11B identifying measured forces between 11 pounds and 111 pounds. In some embodiments, such as the embodiment illustrated in FIG. 11C, the output displayed to a user on a display of a device 200 can be in the form of a force versus time graph. Incorporating a sensor system into a shoe or cast enables a physician, clinical worker, or patient to monitor the amount of pressure on a foot or other limb. In some embodiments, device performance can be read out at the next patient visit. Alternatively, performance can be transmitted to a local server and the Internet to a web site to be analyzed by the clinician.

V. Portable Bathroom Scale.

Surveys and marketing have suggested the popularity of portable scale for consumer to follow weight while traveling. Such a scale could fit within a suitcase or carry-on and weigh less than 8 oz. In order to work, the expectation would be that the accuracy would meet or exceed +/−1%. Due to the very accurate representation of pressure vs raw capacitance from FIG. 4A, such accuracy is achievable from sensor system 100.

Figure 12:
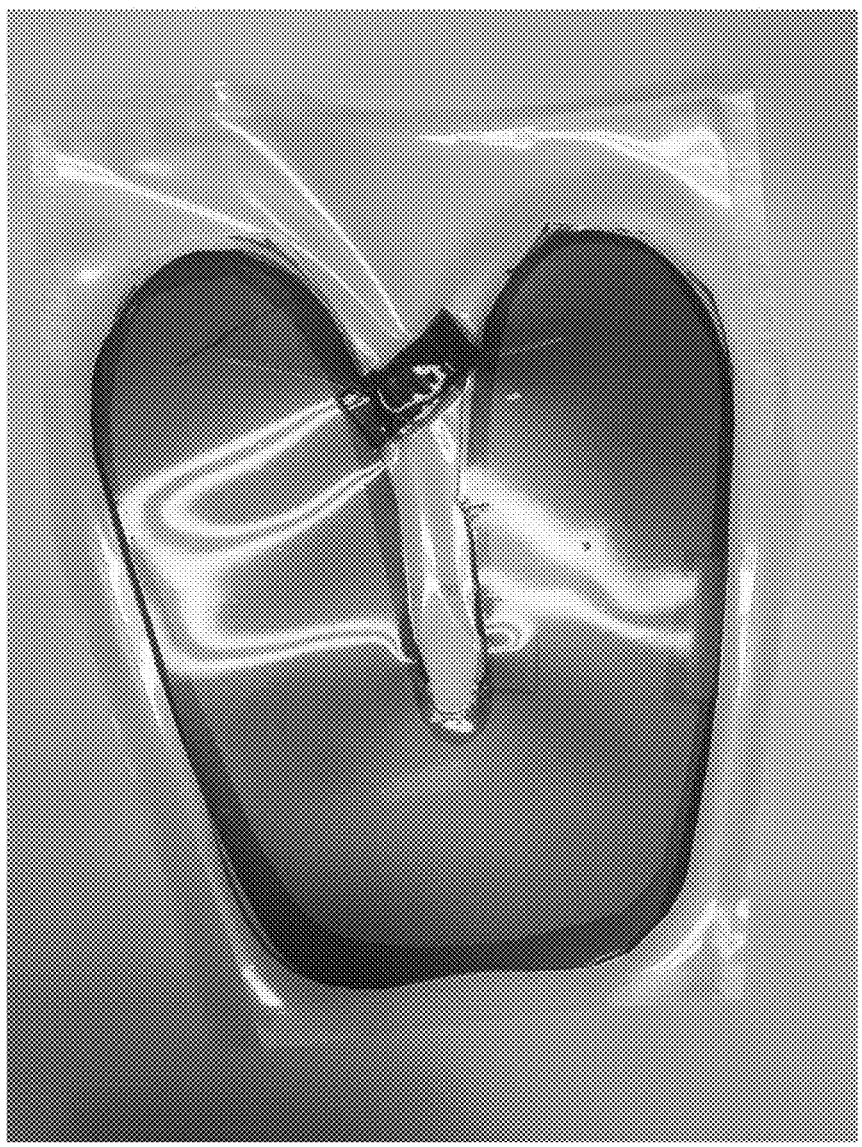
FIG. 12 illustrates one example of a sensor system configured as a weight scale in accordance with some embodiments.

To construct this, two limb load sensors could be arranged or positioned to match normal bilateral standing foot position as shown in FIG. 12. The sensors are connected by the sensor laminate, and there would be a connection via snaps to a transmission unit. The sensors are placed between two thin but rigid polycarbonate or similar plastic with an appealing form factor. This form factor or housing 102 could be foldable. The device is then calibrated to output measurement in units of force by calibrating the units as units of pressure. The combined area of both sensors times pressure are set to equal force, which is then displayed on mobile system 200.

In some embodiments, the plastic envelope is Mylar, which could retain a usable vacuum for >1 year. The electronics 108 can be placed in "deep sleep" between measurements, left on for a short time, and then time out to fall asleep with non-use. This application is more generous with space, so a capacity of 500 ma-hour would be allowed (e.g., Panasonic BR 3032 3 Volt Lithium Coin Cell). This portable scale could operate on the order of one year. However, one of ordinary skill in the art will understand that such descriptions are not limiting and that various configurations can be provided within the scope of this disclosure.

VI. Negative Pressure Sensor

The disclosed sensor system also can be configured to measure negative pressures, which advantageously can be used to monitor negative pressure bandages. Negative pressure bandages are frequently used to help build granulation (e.g., assist in healing) of tissue. This is especially important in healing surgical wounds that have delayed healing.

Figure 13:
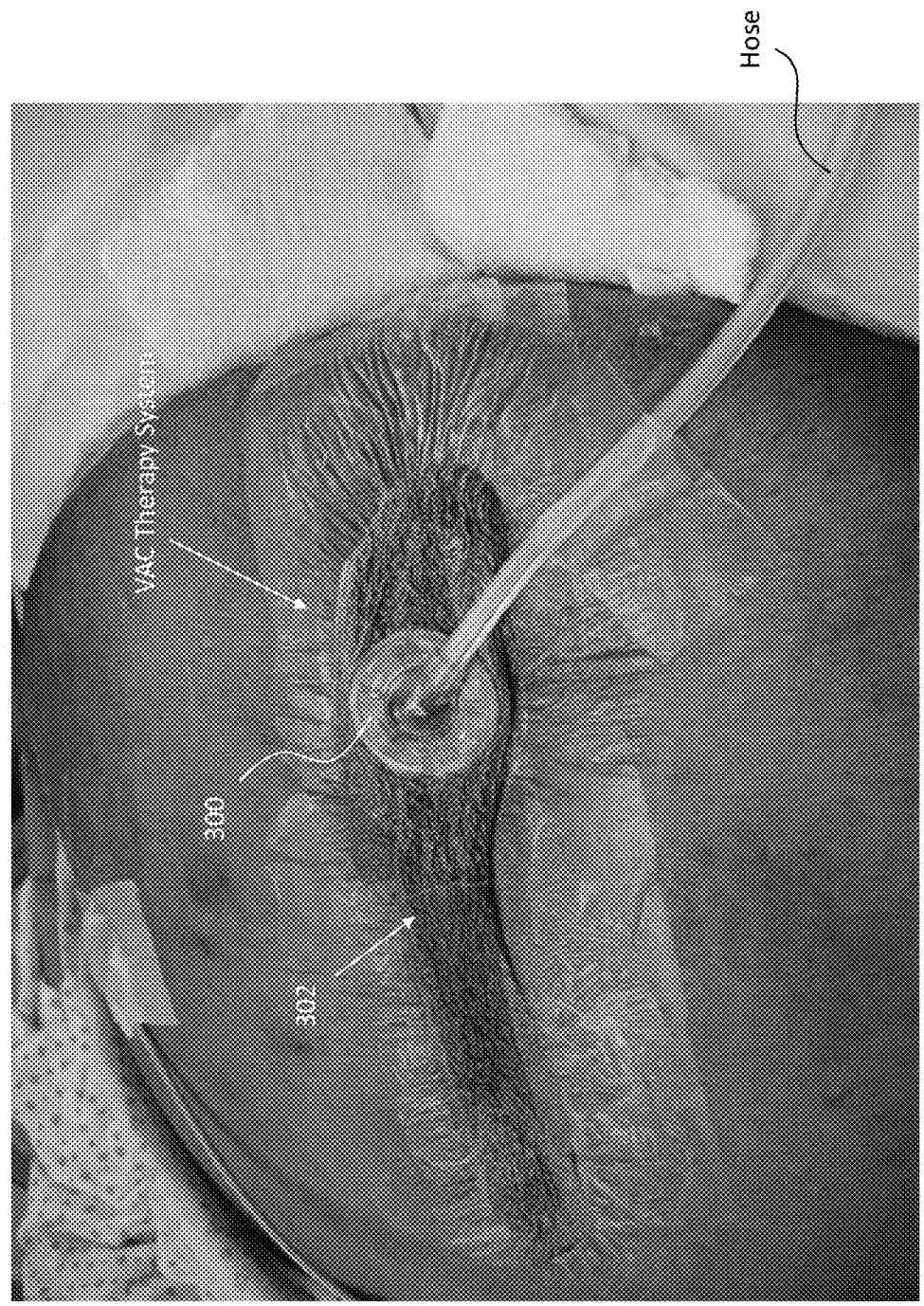
FIG. 13 illustrates a sensor system being used as a negative pressure sensing device in accordance with some embodiments.
Figure 13A:
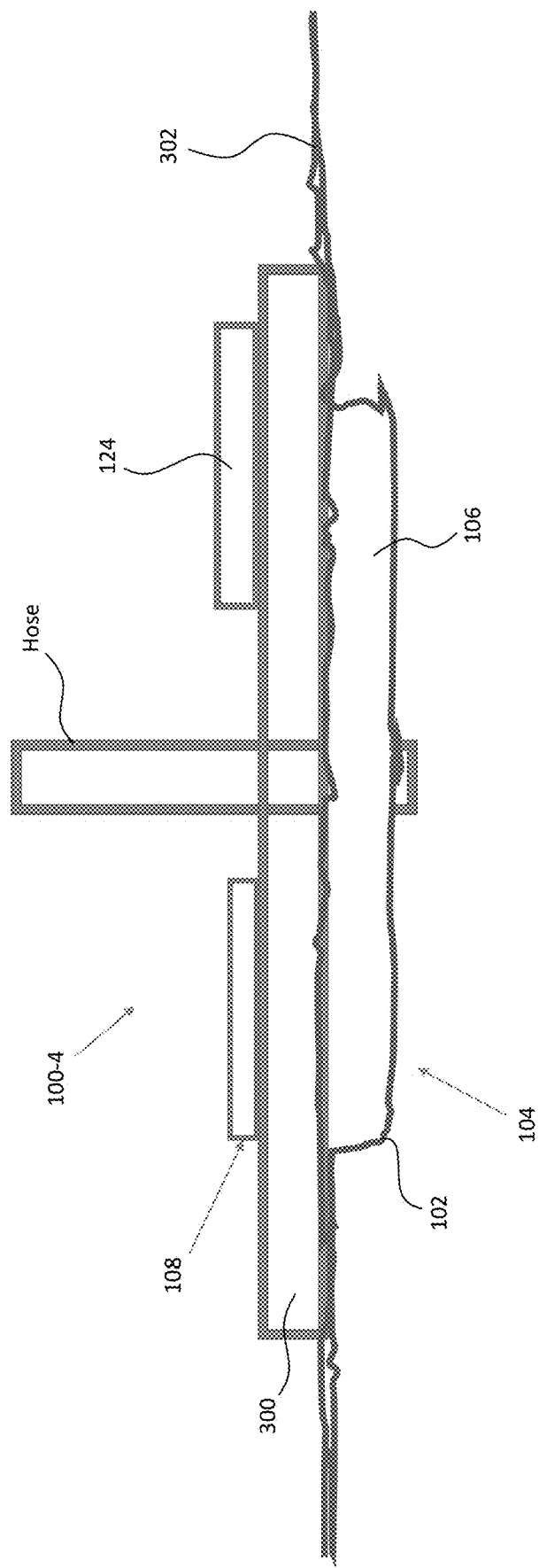
FIGS. 13A-13C are details images of various configurations of a sensor system for use as a negative pressure sensing device in accordance with some embodiments.
Figure 13B:
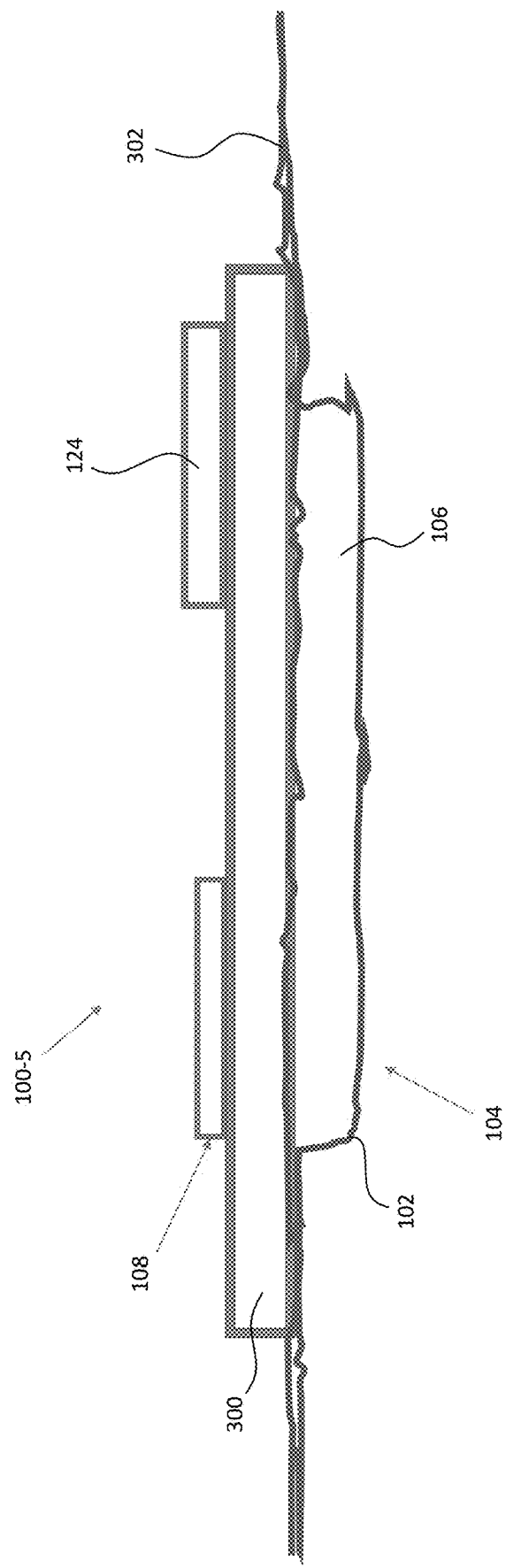
Figure 13C:
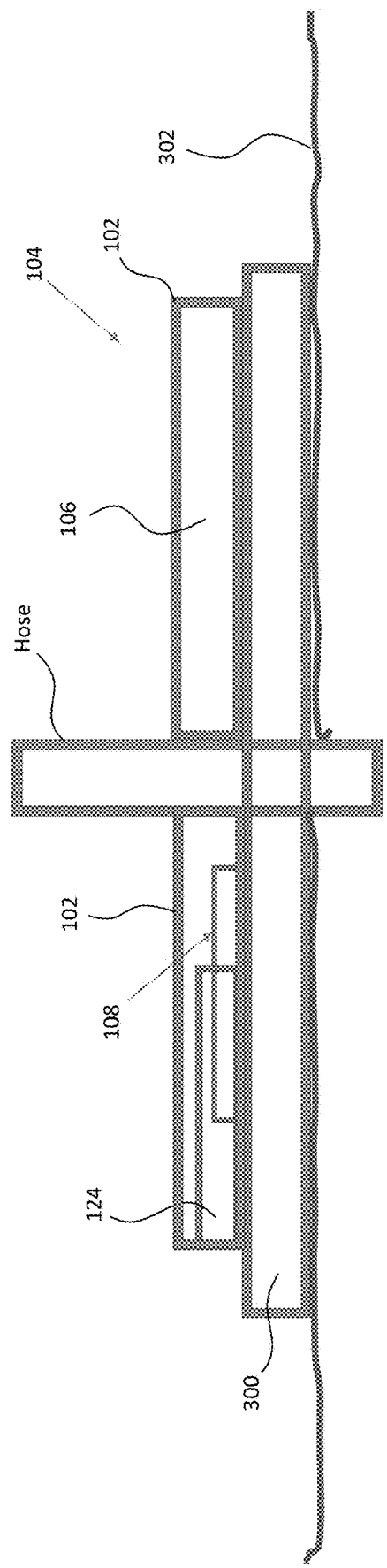

For example, in some embodiments, the sensor is placed beneath a bandage/dressing to which a vacuum is to be applied as shown in FIGS. 13-13C. The relationship between dose of vacuum and healing response is empirically set by the manufacturer. The vacuum is probably inaccurate in many situations. One system, the KCI, uses a "track pad" to connect the bandage interface pressure to the device where it is documented and displayed. (FIG. 13 shows the KCI hose and VAC system for convenience). However, most other systems, such as the Pico and Snap, do not allow measurement of pressure at the bandage interface, but at the vacuum pump at the other end of the connecting tube. Typically, there is no pressure display. Disadvantages are that the vacuum might change with movement or position of the patient. Alternatively, it might not be the same if there are two or more wounds and they are connected by means of a "Y" connector. This negative pressure embodiment could provide confidence that the vacuum system is supplying the correct "dose" continuously at the bandage interface.

The sensor system will output the pressure on the sensor 104, but the software executed by the electronics 108 and/or device 200 is modified to provide an identification of pressure within the bandage/dressing. In some embodiments the electronics 108 for the sensor system 100 are powered by a low capacity Lithium battery due to size constraints. For example, the dimensions of a Lithium coin cell 1216, are 12 mm diameter by 1.6 mm thick. In some embodiments, the electronics can be affixed on atop a disc as shown in FIGS. 13A-13C. In some embodiment, the disc is formed from plastic and has a diameter of 2 cm; however, one of ordinary skill in the art will understand that the disc can be greater or less than 2 cm. This additional thickness imposed by the plastic disc might be no more than 3-4 mm. The ATomega and Bluetooth transmitter would have unique surface mount construction atop this flexible plastic disc as shown in FIG. 13.

In terms of battery drain, one serial pressure reading could be transmitted every 15 minutes, with the electronics 108 "sleeping" in between measurements. With typical use, these devices are employed one week, and then thrown away. The average estimated current drain is 125 μA. If the effective battery capacity is 25 mA-hours, the device would last 180 hours, or 7 days. Additionally, these 640 measurements could be transmitted by Internet or Bluetooth during or between visits to monitor adherence to the pressure prescription.

In some embodiments, the sensor 100 is configured to be used as a negative pressure device. As noted above, FIG. 13 illustrates a negative pressure device in use with a V.A.C. Therapy system available from KCI, an Acelity Company, placed over a wound. At a high level, the V.A.C. Therapy system includes a hose coupled to a plastic disk 300 that is secured over a polyurethane barrier 302. The wound at the center of FIG. 13, beneath the V.A.C. Therapy system, and periwound skin are covered by polyurethane film 302 that creates a vacuum seal. When turned on, the negative pressure system compresses the surrounding soft tissue and foam material, i.e., Granufoam.

The sensor 104 shown in FIG. 13A includes one or more layers 106 of a dielectric foam material formed over the Granufoam wound filler such that sensor system 100-4 retains the foam characteristics. As shown in FIG. 13A, a sensor 104 is positioned within a housing 102 that is vacuum sealed on the internal wound-side of a disk 300 of the V.A.C. Therapy system. Disk 300 in such configurations partially serves as a flexible circuit board for electronics 108 and receives a hose therethrough. Power supply 124 in FIG. 13A can take the form of a disk battery secured to electronics 108. The vacuum pressure would be expressed as the positive pressure caused compression of the foam contents: typically 80-125 mm Hg.

FIG. 13B illustrates another example of a sensor system 100-5 configured as a negative pressure sensor in accordance with some embodiments. As shown in FIG. 13B, a small hole is cut in V.A.C. Therapy system drape 302 and a sensor 104 is attached with skin prep directly to and over the drape 302. Miniaturized electronics 108 can be placed above this on a disk 300 serving as a substrate for electronics 108. The V.A.C. Therapy system drape can then be placed over the sensor 104 of sensor system 100-5. The sensor system 100-5 in this case would measure positive pressure equivalent to vacuum.

FIG. 13C illustrates yet another example of a sensor system 100-6 configured as a negative pressure sensor in accordance with some embodiments. As shown in FIG. 13C, the sensor 104, electronics 108, and power supply 124 are disposed within a rigid shell housing 102 located adjacent and external to the disk 300 of the V.A.C. Therapy system. A port is provided from the hose to housing 102 and the vacuum pressure is output as a negative number.

Figure 14:
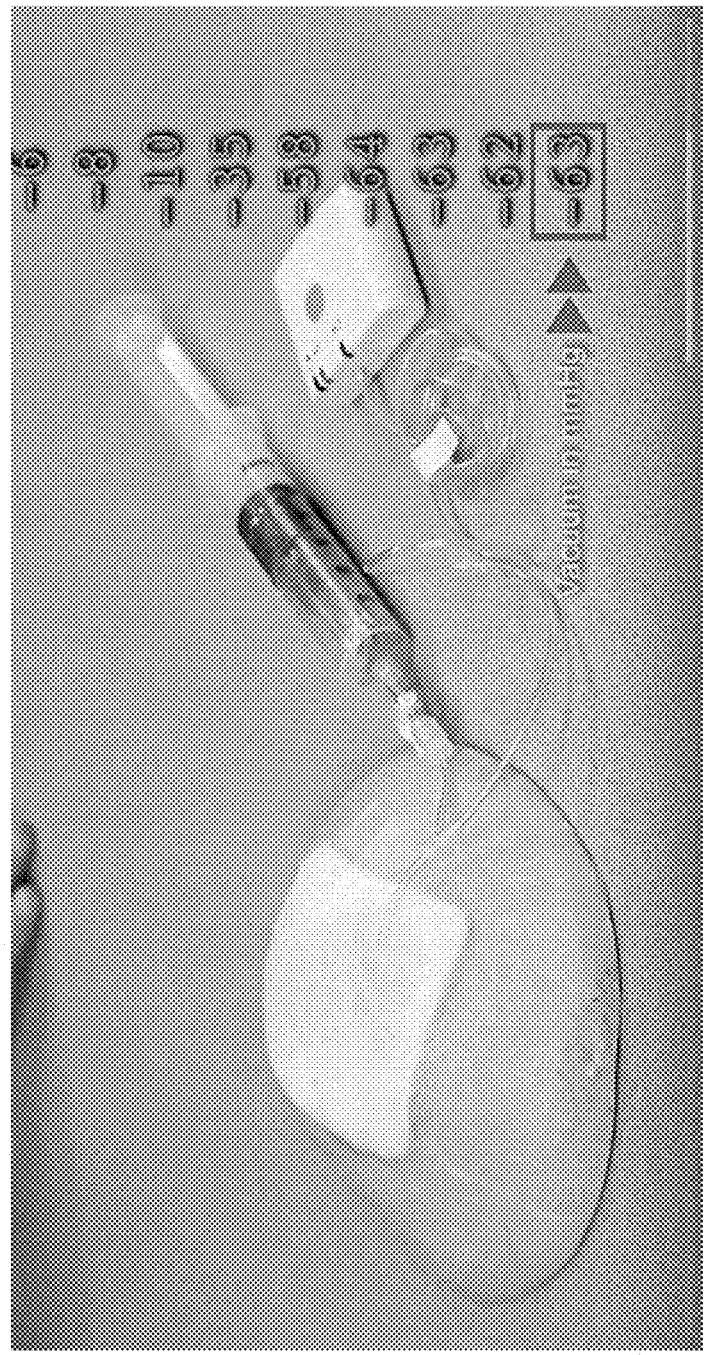
FIG. 14 illustrates another example of a sensor system being used as a negative pressure sensing device in accordance with some embodiments.

FIG. 14 shows an exemplary pressure readout on a device 200 when a sensor system is configured as a negative pressure device in accordance with some embodiments. Here the PICO negative pressure device is connected via tubing to a simulated model wound. A "T" adapter connects this tubing to a 50 cc syringe. Within this syringe is a 1-inch square capacitive sensor connected to the electronics 108. The device transmits the pressure measurement to the mobile device 200. On display 250, the pressure measured: −63 mm Hg, closely matches nominal pressure of −80 mm Hg.

Clinical Trial

A clinical trial was performed to prove the viability of the disclosed system systems. Four compression methods were tested on a sensor system under four different testing conditions. The first condition tested the sensing system when disposed beneath padding, a cohesive layer, and three layers of wrap where each layer of wrap was a three-inch flex wrap available from Medline Industries, Inc. of Northfield, Ill. The second testing condition included position a sensor system padding and four layers of Profore wrapping available from Smith & Nephew, Inc. of Memphis, Tenn. The four layers included a padding layer, a light conforming layer, a light compression and a cohesive layer. The third tested condition included placing a sensing system beneath a double tubular bandage size "E." The fourth tested condition was placing a sensing system beneath a three-layer lymphedema short stretch bandages.

All wraps were applied by experienced clinical staff, including two lymphedema therapists for CDT (Complete Decompressive Therapy) that applied the three-layer lymphedema bandages. The sensor systems were placed on the medial ankle and lower leg for each tested condition. Analysis of variance (ANOVA) was used to determine the overall treatment effect and t-tests for post hoc comparisons between pairs of means. All clinical staff were blind to the results and both left and right legs were used in equal proportion.

Figure 15:
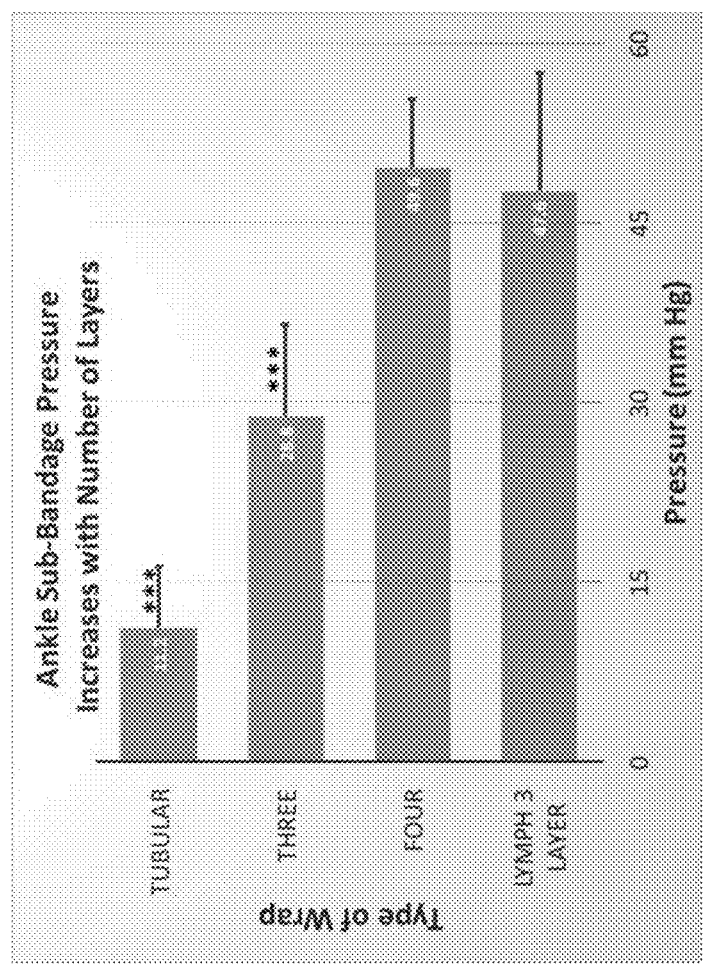
FIG. 15 is a graph representing the results of a clinical trial in which a sensor system in accordance with some embodiments was used to measure the pressure applied by four different types of clinical wraps.

The results, which are shown in FIG. 15, demonstrate a significant difference based on the compression dressing type. The measured pressure of the double tubular bandage was determined to be 11.2±5.1 mm Hg; the measured pressure of the three-layer wrap was 28.8±7.7 mm Hg; the measured pressure of the four-layer wrap was 49.6±5.7; and the measured pressure of the three-layer lymphedema wrap was 47.6±10 mm Hg. The results demonstrate that there were no significant differences between four-layer wraps and the three-layer lymphedema wrap, but on post-hoc t-test comparisons, all other differences were significant. No significant differences were identified based on nurse applier, lymphedema therapist, model, or to which leg the wrap was applied.

The results shown in FIG. 15 generally are consistent with the manufacturer's specifications for each of the tested wraps. For example, the manufacturer specifications for the double tubular wrap states that it applies a pressure between 10-20 mm Hg, and the manufacturer specifications for the three-layer wrap is that the wrap applies a pressure between 20-30 mm Hg. The results for the four-layer wrap were higher than the 42 mm Hg published by Blair (Blair S D, et al., "Sustained Compression and Healing of Chronic Venous Ulcers," British Medical Journal" 297: 1159-1161; 1988). However, the average circumference of the tested ankles of the models was 22 cm, which is small relative to a typical ankle. It is known that smaller ankle circumference is consistent with higher pressures. The lymphedema wraps match published findings (Partsch, H., "Assessing the effectiveness of Multilayer Inelastic Bandaging," Journal of Lymphology, 2:55-61; 2007). Given these results, the study confirms that the capacitive sensor systems verified the predicted differences between the double tubular bandage, three-layer wrap, and four-layer wrap, and therefore provide an accurate measurement and/or monitoring tool.

In some embodiments, a system includes a housing, a capacitive sensor, and an electronics module. The housing has an interior and is configured to be maintained at a first pressure that is lower than a pressure external of the housing the interior under a vacuum pressure. The capacitive sensor is disposed within the housing and includes a plurality of layers of a dielectric material. The electronics module is coupled to the capacitive sensor and includes a processor configured to receive a raw capacitance value from the capacitive sensor and to output a signal identifying a pressure exerted on the capacitive sensor.

In some embodiments, at least one of the plurality of layers of dielectric material includes an open-cell foam material.

In some embodiments, the plurality of layers of a dielectric material include a single layer of material having been folded onto itself at least once.

In some embodiments, the electronics module includes a resistor disposed between the processor and the capacitive sensor.

In some embodiments, the electronics module includes a communications interface for transmitting the signal identifying the pressure exerted on the capacitive sensor to a remote device.

In some embodiments, the first pressure is between −7 and −13.5 PSI relative to ambient pressure at sea level.

In some embodiments, the electronics module is disposed within the housing.

In some embodiments, a system includes a sensor system and a device communicatively coupled to a communications interface of the sensor system. The sensor system includes a capacitive sensor having a plurality of layers of a dielectric material, an electronics module coupled to the capacitive sensor, and a housing. The electronics module includes a processor and the communications interface. The processor is configured to receive a raw capacitance value from the capacitive sensor and cause the communications interface to output a signal identifying a pressure exerted on the capacitive sensor. The housing defines an interior in which at least the capacitive sensor is disposed. The interior of the housing has a pressure that is less than a pressure outside of the housing. The device is configured to receive the signal identifying a pressure exerted on the capacitive sensor and to output a visual indicator of the pressure exerted on the capacitive sensor on a display of the device.

In some embodiments, the device is configured to output an alarm if a value of the signal identifying a pressure exerted on the capacitive sensor is at least one of below or above a threshold.

In some embodiments, the alarm is at least one of an audible alarm, a tactile alarm, and a visual alarm.

In some embodiments, the device is configured to forward the signal identifying the pressure exerted on the capacitive sensor to a server configured to log data.

In some embodiments, at least one of the plurality of layers of dielectric material includes an open-cell foam material.

In some embodiments, the plurality of layers of a dielectric material include a single layer of material having been folded onto itself at least once.

In some embodiments, the electronics module includes a resistor disposed between the processor and the capacitive sensor.

In some embodiments, the raw capacitance value is based on a round trip time of at least one pulse transmitted by the electronics module to be received by the electronics module after passing through the capacitive sensor.

In some embodiments, a method includes transmitting at least one first pulse from an electronics module to a capacitive sensor that is disposed within an interior of a housing that is maintained at a first pressure that is a less than a pressure outside of the housing, the capacitive sensor including a plurality of layers of a dielectric material; receiving, by the electronics module, at least one second pulse from the capacitive sensor; and calculating, using a processor of the electronics module, a pressure exerted on the capacitive sensor based on at least the at least one second pule.

In some embodiments, a method includes transmitting a signal identifying the pressure exerted on the capacitive sensor to a remote device.

In some embodiments, the at least one second pulse passes through a resistor prior to being received by the electronics module.

In some embodiments, the resistor is coupled in series with the capacitive sensor.

In some embodiments, at least one of the plurality of layers of dielectric material includes an open-cell foam material.

In some embodiments, the plurality of layers of a dielectric material include a single layer of material having been folded onto itself at least once.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

SOURCE CODE APPENDIX

```
#include <CapacitiveSensor.h>;
/*
* THIS INCLUDES A COUNTER AND TIME OUT, WHEREIN, IF REACHED,
STOPS ADVERTISING.
* RESET TIMEOUT COUNTER IN 15 MINUTES.
* RESET COMPARISON CAP EVER 25 SECONDS.
*
    CapacitiveSensor cs_5_2 = CapacitiveSensor(5,2); // 1M resistor between pins 5 &
2, pin 2 is sensor pin, add a wire and or foil if desired
    const int numReadingsforloop = 50;
    long readingsforloop[numReadingsforloop];
    float averageforloop = 0;
    long totalforloop = 0;
    long total1Min = 0;
    float gain = 0;
    float gainsquare = 0;
    float gainsquare1000 = 0;
    long total1average = 0;
    long total1averagesquare = 0;
    long total1averageraw = 0;
    long total1 = 0;
    int Time_out = 200; //timeout in 15 minutes.
    int message = 0; // This will hold one byte of the serial message
    float zero = 0;
    long total1baseline = 0;
    long total1averagebaseline = 0;
    int total1averageref =0;
    int Sample_trigger = 25;
    int i = 0;
    int j = 0;
    int dif = 0;
    bool disconnect;
void setup( )
{
    //cs_5_2.set_CS_AutocaL_Millis(10000000); // turn off autocalibrate on channel 1 -
just as an example -- also am using Raw data
        Serial.begin( );
        if (Bean.getAccelerationRange( ) != 8) {
        Bean.setAccelerationRange(8);
        }
        if (Bean.getAccelerometerPowerMode( ) != VALUE_LOW_POWER_100MS) {
        Bean.setAccelerometerPowerMode(VALUE_LOW_POWER_ 100MS);
        }
        Bean.enableWakeOnConnect(true); //Wake up if connected
        Bean.enableMotionEvent(DOUBLE_TAP_EVENT);
        gain = 0.1948;
        gainsquare = -0.00004; ,
        for (int readIndexforloop = 0; readIndexforloop < numReadingsforloop;
readIndexforloop++)
    {
        total1baseline = cs_5_2.capacitiveSensorRaw(30);
        readingsforloop[readIndexforloop] = total1baseline;
        totalforloop= totalforloop+ readingsforloop[readIndexforloop];
        delay(10);
    }
        total1averagebaseline=totalforloop/numReadingsforloop;
        }
void loop( )
    {
        total1average = 0;
        totalforloop = 0;
        for (int readIndexforloop = 0; readIndexforloop < numReadingsforloop;
readIndexforloop++)
    {
        total1 = 0;
        total1 = cs_5_2.capacitiveSensorRaw(30);
        readingsforloop[readIndexforloop] = total1;
        totalforloop= totalforloop+ readingsforloop[readIndexforloop];
        delay(10);
    }
        total1average=totalforloop/numReadingsforloop;
        total1averageraw = total1average;
        total1average=total1average-total1averagebaseline;
        total1averagesquare=total1average*total1average;
        total1average=total1averagesquare*gainsquare+total1average*gain;
        i= i + 1; // advances registers
        j= j + 1;
        if(i == 1000)
        {i = 0;} //resets counter
```

-continued

SOURCE CODE APPENDIX

```
    if(j == 25) // reset reference every 25 secods.
    {j = 0;
    total1averageref = total1average;}
    delay(50); // arbitrary delay to limit data to serial port
Serial.println(total1average); // print sensor output 1
        dif = total1average - total1averageref;
if(dif > 10 or dif < -10) //if capacitance differenc >10 pF, reset timeout counter.
{i = 0;}
    if (Serial.available( ) > 0) { // Check if there is a new message
        message = Serial.read( ); // Put the serial input into the message
    if (message == 'S'){ // If a capitol S is received...
        Serial.println("Going to sleep");
        Bean.sleep(1000000);
    }
    if (message == 'G'){
        gainsquare1000 = gainsquare*1000;
        Serial.print("Gain =");
        Serial.println(gain);Serial.print("Gainsquare*1000 =");
        Serial.println(gainsquare1000);
        gainsquare1000=0; }
    if (message == 'C'){
        Serial.print("Raw Capacitance =");
        Serial.println(total1averageraw);}
    if (message == 'I'){
        Serial.print("i =");
        Serial.println(i);
        Serial.print("j =");
        Serial.println(j);}
    if (message == 'V'){
        Serial.println("Version = V19 timeout capchange accelerometer interupt");
    }
    if (message == 'T'){
        Serial.print("Time_out =");
        Serial.println(Time_out);
    }
    if (message == 'A'){
        Serial.println("What is new gain?"); //Prompt User for input
        while (Serial.available( )==0) {
    }
    gain=Serial.parseFloat( ); //Read user input into gain
        Serial.println("What is new gainsquare?"); //Prompt User for input
        while (Serial.available( )==0) {
        }
        gainsquare=Serial.parseFloat( );
    }
        if (message == 'R'){
        Serial.println("Resetting baseline");
        total1averagebaseline = total1averageraw;
        //Serial.print("total1average");
        //Serial.println(total1average);
        //Serial.print("total1averagebaseline");
        //Serial.println(total1averagebaseline);
        }
if (message == 'D'){ // If a capitol D is received...
    Serial.println("20 sec to disconnect");
    delay(20000);
    Bean.disconnect( ); //does not help with bluetooth connection problem, but stops loop
from progressing; may be good for time out
    delay(20000);
    Bean.setLed(0, 0, 255);
    Bean.sleep(30000);//Allow to disconnect during this 20 second of sleep.
    Bean.setLed(0, 0, 0);
    //attachPinChangeInterrupt(0, pinChanged, FALLING);
    Bean.enableAdvertising(false);
    // Disable advertising.
    // Sleep all the time when not hjandling an interrupt
    Bean.sleep(0xFFFFFFFF);
    //Bean.setLed(255, 0, 0);
    Bean.checkMotionEvent(DOUBLE_TAP_EVENT);
    //Bean.sleep(5000);
    //Bean.setLed(0, 0, 0);
    Bean.enableAdvertising(true);
    // Enable advertising and set the LED to green.
    Bean.setLed(0, 255, 0);
    Bean.sleep(30000);
    // Sleep for 30 seconds
    Bean.setLed(0, 0, 0);
```

-continued

SOURCE CODE APPENDIX

```
    }
   }
// Bean.sleep(3000);
      if (i == Time_out){ // If timeout is reached stop advertising
Serial.println("20 sec to disconnect");
i =0;
delay(20000);
Bean.disconnect( ); //does not help with bluetooth connection problem, but stops loop
from progressing; may be good for time out
delay(20000);
Bean.setLed(0, 0, 255);
Bean.sleep(30000);//Allow to disconnect during this 20 second of sleep.
Bean.setLed(0, 0, 0);
//attachPinChangeInterrupt(0, pinChanged, FALLING);
Bean.enableAdvertising(false);
// Disable advertising.
// Sleep all the time when not hjandling an interrupt
Bean.sleep(0xFFFFFFFF);
Bean.checkMotionEvent(DOUBLE_TAP_EVENT);
//Bean.setLed(255, 0, 0);
//Bean.sleep(5000);
//Bean.setLed(0, 0, 0);
Bean.enableAdvertising(true);
// Enable advertising and set the LED to green.
Bean.setLed(0, 255, 0);
Bean.sleep(30000);
// Sleep for 30 seconds
Bean.setLed(0, 0, 0);
   }
}
```

What is claimed is:

1. A system, comprising:
a sealed, flexible housing having an interior configured to be maintained at a first pressure that is lower than ambient pressure external of the housing;
a capacitive sensor disposed within the interior of the housing, the capacitive sensor including a plurality of layers of a dielectric material; and
an electronics module coupled to the capacitive sensor, the electronics module including a processor configured to receive a raw capacitance value from the capacitive sensor and to output a signal identifying a pressure exerted on the capacitive sensor.

2. The system of claim 1, wherein at least one of the plurality of layers of dielectric material includes an open-cell foam material.

3. The system of claim 1, wherein the plurality of layers of a dielectric material include a single layer of material having been folded onto itself at least once.

4. The system of claim 1, wherein the electronics module includes a resistor disposed between the processor and the capacitive sensor.

5. The system of claim 1, wherein the electronics module includes a communications interface for transmitting the signal identifying the pressure exerted on the capacitive sensor to a remote device.

6. The system of claim 1, wherein the first pressure is between −7 and −13.5 PSI relative to ambient pressure at sea level.

7. The system of claim 1, wherein the electronics module is disposed within the housing.

8. A system, comprising:
a sensor system, the sensor system including:
a capacitive sensor having a plurality of layers of a dielectric material,
an electronics module coupled to the capacitive sensor, the electronics module including a processor and a communications interface, the processor configured to receive a raw capacitance value from the capacitive sensor and cause the communications interface to output a signal identifying a pressure exerted on the capacitive sensor, and
a housing defining an interior in which at least the capacitive sensor is disposed, the interior of the housing having a pressure that is less than a pressure outside of the housing; and
a device communicatively coupled to the communications interface of the sensor system, the device configured to receive the signal identifying a pressure exerted on the capacitive sensor and to output a visual indicator of the pressure exerted on the capacitive sensor on a display of the device.

9. The system of claim 8, wherein the device is configured to output an alarm if a value of the signal identifying a pressure exerted on the capacitive sensor is at least one of below or above a threshold.

10. The system of claim 9, wherein the alarm is at least one of an audible alarm, a tactile alarm, and a visual alarm.

11. The system of claim 8, wherein the device is configured to forward the signal identifying the pressure exerted on the capacitive sensor to a server configured to log data.

12. The system of claim 8, wherein at least one of the plurality of layers of dielectric material includes an open-cell foam material.

13. The system of claim 8, wherein the plurality of layers of a dielectric material include a single layer of material having been folded onto itself at least once.

14. The system of claim 8, wherein the raw capacitance value is based on a round trip time of at least one pulse transmitted by the electronics module to be received by the electronics module after passing through the capacitive sensor.

15. A method, comprising:
- transmitting at least one first pulse from an electronics module to a capacitive sensor that is disposed within an interior of a sealed, flexible housing that is maintained at a first pressure that is a less than ambient pressure outside of the housing, the capacitive sensor including a plurality of layers of a dielectric material;
- receiving, by the electronics module, at least one second pulse from the capacitive sensor; and
- calculating, using a processor of the electronics module, a pressure exerted on the capacitive sensor based on at least the at least one second pulse.

16. The method of claim 15, further comprising transmitting a signal identifying the pressure exerted on the capacitive sensor to a remote device.

17. The method of claim 15, wherein the at least one second pulse passes through a resistor prior to being received by the electronics module.

18. The method of claim 17, wherein the resistor is coupled in series with the capacitive sensor.

19. The method of claim 15, wherein at least one of the plurality of layers of dielectric material includes an open-cell foam material.

20. The method of claim 19, wherein the plurality of layers of a dielectric material include a single layer of material.

\* \* \* \* \*